United States Patent
Brockschmidt

(10) Patent No.: US 10,668,179 B2
(45) Date of Patent: *Jun. 2, 2020

(54) SYSTEMS AND METHODS FOR POWERING A LOAD

(71) Applicant: The Boeing Company, Chicago, IL (US)

(72) Inventor: Arthur E. Brockschmidt, Renton, WA (US)

(73) Assignee: The Boeing Company, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/141,560

(22) Filed: Sep. 25, 2018

(65) Prior Publication Data

US 2019/0290795 A1    Sep. 26, 2019

Related U.S. Application Data

(60) Provisional application No. 62/645,888, filed on Mar. 21, 2018.

(51) Int. Cl.
*A61L 2/24* (2006.01)
*G01J 1/42* (2006.01)
(Continued)

(52) U.S. Cl.
CPC .......... *A61L 2/24* (2013.01); *A61L 2/10* (2013.01); *G01J 1/429* (2013.01); *H05B 41/3922* (2013.01); *H05B 47/105* (2020.01)

(58) Field of Classification Search
CPC ............ H05B 33/0815; H05B 33/0845; H05B 37/02; H05B 33/0818; H05B 41/2822;
(Continued)

(56) References Cited

U.S. PATENT DOCUMENTS

| 5,483,127 A | 1/1996 | Widmayer |
| 5,705,898 A | 1/1998 | Yamashita et al. |

(Continued)

FOREIGN PATENT DOCUMENTS

| DE | 198 24 423 | 12/1999 |
| JP | H08 31585 | 2/1996 |

(Continued)

OTHER PUBLICATIONS

Co-pending U.S. Appl. No. 15/632,968, filed Jun. 26, 2017.
(Continued)

*Primary Examiner* — Wei (Victor) Y Chan
(74) *Attorney, Agent, or Firm* — McDonnell Boehnen Hulbert & Berghoff LLP

(57) ABSTRACT

In an example, a power factor corrector (PFC) including a first PFC input, a second PFC input, and a PFC output. The first PFC input is configured to receive an input power from a power source. The second PFC input is configured to receive a signal from a feedback circuit. The PFC output configured to output a direct current (DC) power, which is based on the input power at the first PFC input and the signal at the second PFC input. The feedback circuit is coupled to the PFC output and the second PFC input. The feedback circuit is configured to provide the signal at the second PFC input based on an input parameter related to a condition that is sensible by a sensor. The condition is related to operation of a load.

20 Claims, 11 Drawing Sheets

(51) Int. Cl.
  *A61L 2/10*    (2006.01)
  *H05B 41/392*  (2006.01)
  *H05B 47/105*  (2020.01)
  *H05B 37/02*   (2006.01)

(58) Field of Classification Search
  CPC ............ H05B 41/2824; H05B 33/0851; H05B 33/0884; H05B 41/382; H05B 33/0857
  USPC .......................................... 315/291, 224, 247
  See application file for complete search history.

(56) References Cited

U.S. PATENT DOCUMENTS

| | | | |
|---|---|---|---|
| 6,877,248 B1 | 4/2005 | Cross et al. | |
| 8,084,752 B2 | 12/2011 | Ranta et al. | |
| 8,138,690 B2 | 3/2012 | Chemel et al. | |
| 8,339,069 B2 | 12/2012 | Chemel et al. | |
| 8,368,321 B2 | 2/2013 | Chemel et al. | |
| 8,543,249 B2 | 9/2013 | Chemel et al. | |
| 8,552,664 B2 | 10/2013 | Chemel et al. | |
| 8,593,135 B2 | 11/2013 | Chemel et al. | |
| 8,805,550 B2 | 8/2014 | Chemel et al. | |
| 8,954,170 B2 | 2/2015 | Chemel et al. | |
| 9,623,133 B2 | 4/2017 | Childress et al. | |
| 9,700,072 B2 | 7/2017 | Dobrinsky et al. | |
| 9,783,974 B1 | 10/2017 | Tillotson | |
| 9,855,353 B1 | 1/2018 | Stacy | |
| 9,993,571 B2 | 6/2018 | Lin et al. | |
| 10,130,727 B1 | 11/2018 | Byrnes et al. | |
| 10,145,055 B1 | 12/2018 | Harlan et al. | |
| 2002/0145041 A1* | 10/2002 | Muthu ............... H05B 33/0815 235/454 | |
| 2006/0087259 A1 | 4/2006 | Fiorello | |
| 2006/0163135 A1 | 7/2006 | Ellis et al. | |
| 2010/0193629 A1 | 8/2010 | Breit et al. | |
| 2011/0057123 A1 | 3/2011 | Ho | |
| 2011/0155915 A1 | 6/2011 | Brueck et al. | |
| 2012/0161629 A1 | 6/2012 | Kim et al. | |
| 2013/0049624 A1* | 2/2013 | Umezawa ............... H05B 41/28 315/224 |
| 2013/0330235 A1 | 12/2013 | Stibich et al. | |
| 2014/0059796 A1 | 3/2014 | Boodaghians et al. | |
| 2014/0266695 A1 | 9/2014 | Addison et al. | |
| 2016/0195427 A1 | 7/2016 | Vance et al. | |
| 2016/0220716 A1 | 8/2016 | Childress et al. | |
| 2016/0250362 A1 | 9/2016 | Mackin | |
| 2017/0107659 A1 | 4/2017 | Hills | |
| 2017/0279300 A1* | 9/2017 | Catalano ............... H02J 7/0068 |
| 2017/0283062 A1 | 10/2017 | Childress | |
| 2017/0283092 A1 | 10/2017 | Brown et al. | |
| 2017/0284076 A1 | 10/2017 | Jensen | |
| 2018/0050122 A1 | 2/2018 | Lin et al. | |
| 2018/0051447 A1 | 2/2018 | Hills et al. | |
| 2018/0064833 A1 | 3/2018 | Childress et al. | |
| 2018/0079528 A1 | 3/2018 | Siegmeth et al. | |
| 2018/0084956 A1 | 3/2018 | Childress | |
| 2018/0369434 A1 | 12/2018 | Callahan | |
| 2018/0369439 A1 | 12/2018 | Brockschmidt et al. | |
| 2018/0371733 A1 | 12/2018 | Childress et al. | |
| 2018/0373157 A1 | 12/2018 | Kimsey-Lin | |
| 2019/0171111 A1 | 6/2019 | Kimsey-Lin | |

FOREIGN PATENT DOCUMENTS

| | | |
|---|---|---|
| JP | 2002263645 | 9/2002 |
| WO | 99/62567 | 12/1999 |

OTHER PUBLICATIONS

Co-pending U.S. Appl. No. 15/633,028, filed Jun. 26, 2017.
Co-pending U.S. Appl. No. 15/633,085, filed Jun. 26, 2017.
Co-pending U.S. Appl. No. 15/633,121, filed Jun. 26, 2017.
Co-pending U.S. Appl. No. 15/633,142, filed Jun. 26, 2017.
Co-pending U.S. Appl. No. 16/141,539, filed Sep. 25, 2018.
Extended European Search Report prepared by the European Patent Office in application No. EP 19 16 4482.2 dated Aug. 21, 2019.

* cited by examiner

SYSTEMS AND METHODS FOR POWERING A LOAD

CROSS-REFERENCE TO RELATED APPLICATIONS

The present application claims priority to U.S. Provisional Patent Application No. 62/645,888, filed on Mar. 21, 2018, which is hereby incorporated by reference in its entirety.

FIELD

The present disclosure generally relates to systems and methods for powering a load, and more particularly to systems and methods for dynamically adjusting a power supplied to the load based on conditions that may affect operation of the load. Such loads may include (but are not constrained to) loads that can benefit from an adjustable power supply, such as an ultraviolet (UV) light source.

BACKGROUND

Pathogens may be spread between humans, between animals, or between humans and animals in many different ways. Consequently, there is an increasing need for the disinfection of public environments. One approach for disinfecting an environment involves irradiating the environment with ultraviolet (UV) light using a UV light source.

SUMMARY

In an example, a power factor corrector (PFC) includes a first PFC input, a second PFC input, and a PFC output. The first PFC input is configured to receive an input power from a power source. The second PFC input is configured to receive a signal from a feedback circuit. The PFC output configured to output a direct current (DC) power, which is based on the input power at the first PFC input and the signal at the second PFC input. The feedback circuit is coupled to the PFC output and the second PFC input. The feedback circuit is configured to provide the signal at the second PFC input based on an input parameter related to a condition that is sensible by a sensor. The condition is related to operation of a load.

In another example, a power control module includes a first input, a second input, and an output. The first input is configured to receive an input power from a power source. The second input is configured to receive a signal from a feedback module. The output is configured to output to a supply power, which is based on the input power at the first input and the signal at the second input. The feedback module is coupled to the output and the second input. The feedback module is configured to provide the signal at the second input based on an input parameter related to a condition that is sensible by a sensor. The condition is related to operation of a load.

In another example, a power buffer includes an input, an energy storage device, an output, and a control terminal. The input is configured to receive an electrical power from a PFC during a first portion of a time interval. The energy storage device is configured to store the electrical power received at the input during the first portion of the time interval. The output is configured to be coupled to a pulse-width modulator (PWM). The output is configured to, during a second portion of the time interval, output the electrical power stored in the energy storage device during the first portion of the time interval. The control terminal is configured to receive, from a control device, a control signal for controlling operation of the energy storage device.

The features, functions, and advantages that have been discussed can be achieved independently in various embodiments or may be combined in yet other embodiments further details of which can be seen with reference to the following description and drawings.

BRIEF DESCRIPTION OF THE FIGURES

The novel features believed characteristic of the illustrative embodiments are set forth in the appended claims. The illustrative embodiments, however, as well as a preferred mode of use, further objectives and descriptions thereof, will best be understood by reference to the following detailed description of an illustrative embodiment of the present disclosure when read in conjunction with the accompanying drawings, wherein:

DETAILED DESCRIPTION

Figure 1:
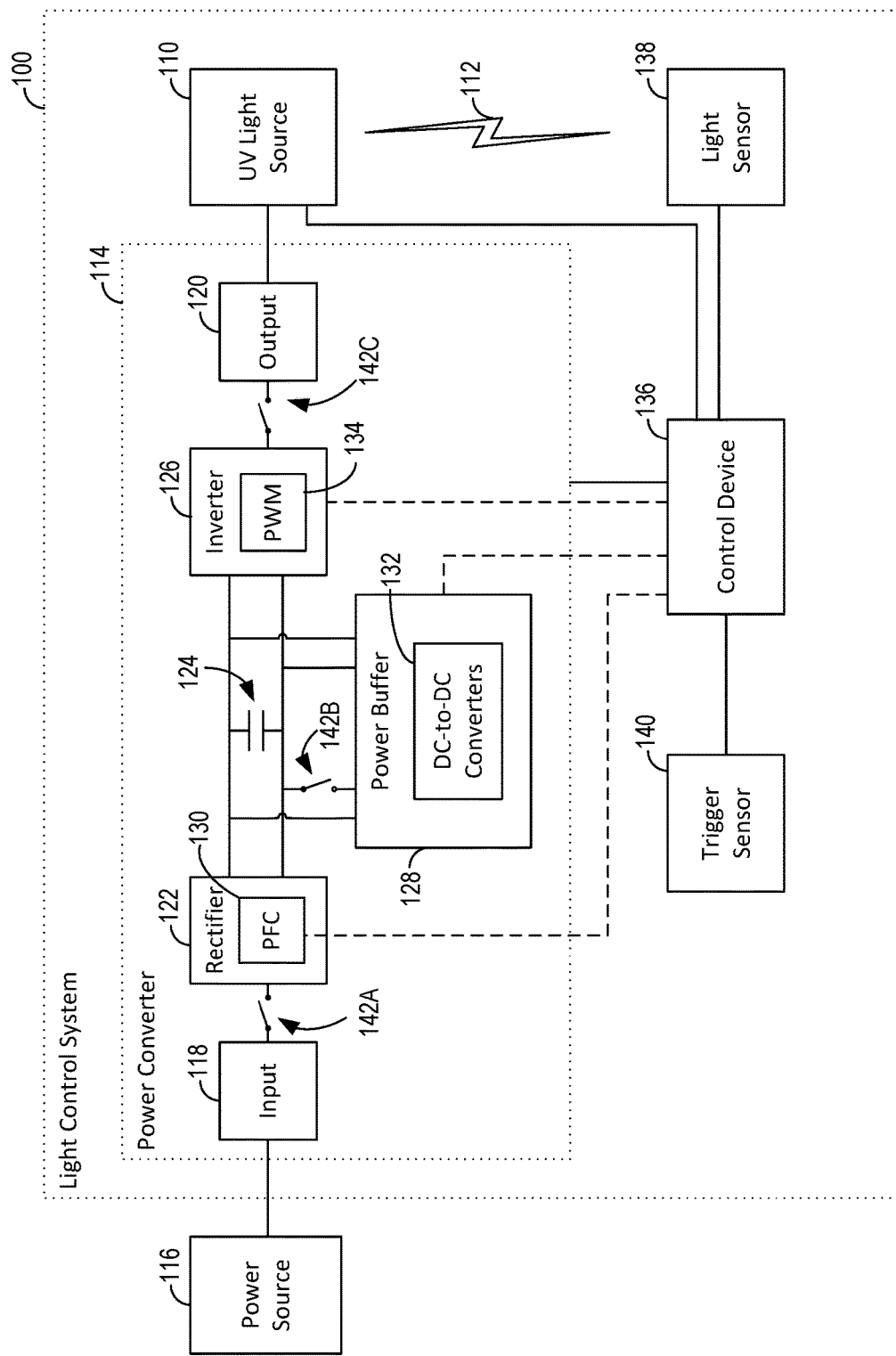
FIG. 1 illustrates a simplified block diagram of a light control system according to an example embodiment.

Disclosed embodiments will now be described more fully hereinafter with reference to the accompanying drawings, in which some, but not all of the disclosed embodiments are shown. Indeed, several different embodiments may be described and should not be construed as limited to the embodiments set forth herein. Rather, these embodiments are described so that this disclosure will be thorough and complete and will fully convey the scope of the disclosure to those skilled in the art.

The systems and methods of the present disclosure provide power supply control systems for supplying a dynamically adjustable level of power to a load to, for instance, operate the load at a target level of operational output over time and/or over a series of activation cycles of the load. As described in further detail below, in some examples, the load may experience degraded operational output due to, for instance, changes in the load and/or changed conditions in an environment in which the load operates. The systems and methods of the present disclosure can sense such changes and provide feedback to one or more components of a power supply control system to dynamically adjust an electrical parameter of a supply power provided to the load. In this way, the systems and methods of the present application can compensate for changes in the load and/or the environment over time and/or the series of activation cycles.

In some examples, the systems and methods of the present disclosure provide light control systems and methods for operating a UV light source to achieve a target level of antimicrobial efficacy over a series of activation cycles. When activated during an activation cycle, the UV light source emits UV light, which can kill and/or disable microorganisms such as bacteria, viruses, molds, and/or other pathogens. For example, when microorganisms are exposed to a sufficiently high dose of UV light, the UV light can damage nucleic acids and/or disrupt the deoxyribonucleic acid (DNA) of the microorganisms, rendering the microorganisms unable to carry out cellular functions and infect people.

The antimicrobial efficacy of the UV light during the activation cycle is related to factors such as, for instance, the length of time a microorganism is exposed to the UV light (i.e., the "exposure time"), the intensity of the UV light, and the wavelength of the UV light. As one example, the antimicrobial efficacy of the UV light at a particular wavelength can be specified as a UV dose, which can be determined based on an equation having the general form of:

$$\text{UV dose} = \text{UV light intensity} \times \text{exposure time} \quad \text{(eq. 1)}$$

where the UV dose is specified in $mWs/cm^2$, the UV light intensity is specified in $mW/cm^2$ at a predetermined distance (e.g., one meter) from the UV light source, and the exposure time is specified in seconds.

Over time, the intensity of the UV light emitted by the UV light source declines due to, for example, lamp lumen depreciation (LLD) and/or lamp dirt depreciation (LDD). For instance, LLD can be caused by chemical reactions, which can deposit light-absorbing particles within the UV light source, over multiple activation cycles. Whereas, LDD can be caused by an accumulation of debris (e.g., dirt and/or dust particles) on an exterior surface of the UV light source, which block UV light emission.

Additionally, for example, the intensity of the UV light emitted by the UV light source can be affected by the temperature of the UV light source. For instance, the temperature of the UV light source can vary due to changes in an ambient temperature of an environment in which the UV light source is operating, and/or due to heat resulting from operation of the UV light source itself. Accordingly, because the intensity of the UV light source changes over multiple activation cycles, it can be challenging to maintain the target level of antimicrobial efficacy throughout the life of the UV light source. Other environmental factors may also affect operation of the UV light source over the life of the UV light source.

The example systems and methods described herein can beneficially overcome challenges to operating a UV light source at a target level of antimicrobial efficacy over multiple activation cycles and/or the life of the UV light source. In particular, the systems and methods can dynamically adjust an electrical parameter of a supply power provided to the UV light source to compensate for changes in the intensity of the UV light and/or other operating conditions over a series of activation cycles.

Within examples, a light control system can include a power converter, a light source, one or more sensors, and a control device. The power converter can provide a supply power to the light source, which the light source can use to emit light during a series of activation cycles. The sensor(s) can sense a condition related to operation of the light source, and provide to the control device a sensor signal indicting an input parameter related to the condition sensed by the sensor(s). The control device can provide a feedback signal to the power converter to cause the power converter to adjust, based on the input parameter, an electrical parameter of the supply power.

Also, within examples, the power converter can include a plurality of modules that are operable to convert an input power received from a power source to the supply power having the electrical parameter. In some examples, the control device can provide the feedback signal to one or more of the modules to selectively those module(s) to adjust the electrical parameter of the power supply responsive to changes in the operating conditions that may affect operation of the light source. Additionally, as described in further detail below, the control device can be separate from the sensor(s) and/or integrated with the sensors in example embodiments. As such, the sensor(s) can sense the operating conditions and responsively communicate, directly and/or indirectly, with the modules of the power converter to adjust the electrical parameter of the supply power.

Also, within examples, the systems and methods of the present application can provide for operating the UV light source (or another load) in a limited-power environment. Because the UV light source converts electrical power into the UV light, the UV light source may require at least a threshold amount of power to emit the UV light at the intensity and/or for the exposure time providing the target level of antimicrobial efficacy. The threshold amount of power required to emit the UV light at the target level of antimicrobial efficacy may be based on characteristics of the UV light source such as, for example, a type of UV light source, and/or a size of the UV light source.

In a limited-power environment, a power source and/or an electrical distribution system may provide a power that is insufficient by itself for activating the UV light source to emit the UV light at the target level of antimicrobial efficacy (e.g., at a target intensity of the UV light). In one example, the UV light source can be coupled to a power source, which is configured to generate a power that is less than the threshold amount of power required by the UV light source to emit the UV light at the target level of antimicrobial efficacy. For instance, the UV light source can be installed in an environment in which it is desirable to reduce (or minimize) the size and/or weight of the power source.

In another example, the power source may be configured to generate a sufficient amount of power, but an electrical distribution system may supply portions of the generated power to other systems as well such that only an insufficient portion of the power is available to the UV light source. For instance, a vehicle can have an electrical distribution system that provides specific portions of a power supplied by a power source to various subsystems of the vehicle in accordance with a power budget. In this way, each subsystem receives an amount of power that is sufficient to meet its needs. A problem is presented, however, when the vehicle is to be retrofitted with the UV light source as the power requirements of the UV light source may not have been taken into consideration when the power budget and electrical distribution system were designed.

As noted above, the systems and methods described herein can also beneficially overcome challenges to operating the UV light source at the target level of antimicrobial efficacy in a limited-power environment (e.g., a vehicle and/or an aircraft lavatory). For instance, within examples, a light control system can receive an input power from a power source during a time interval. A UV light source of the light control system is deactivated during a first portion of the time interval, and the UV light source is activated to emit UV light during a second portion of the time interval. However, the input power received during the second portion of the time interval is insufficient by itself for activating the UV light source to emit the UV light at the target level of antimicrobial efficacy.

To address this limitation of the input power, the light control system can store the input power in a power buffer during the first portion of the time interval. Later, during the second portion of the time interval, the light control system can provide to the UV light source a supply power that combines (i) the input power received during the second portion of the time interval and (ii) the power stored in the power buffer during the first portion of the time interval. The combination of power is sufficient for activating the UV light source to emit the UV light at the target level of antimicrobial efficacy.

Within examples, the light control system described herein can be located in any environment having a power supply, which can benefit from disinfection. For instance, the light control system can be in a vehicle (e.g., an aircraft, a boat, a train, an automobile, an unmanned vehicle, a transportation vehicle with both ground and non-ground capabilities, an unmanned vehicle, and/or an air-cargo vehicle), a medical environment (e.g., a hospital, a doctor office, and/or other healthcare facility), a restaurant, an office, and/or a household. In one implementation, the light control system can be located in a lavatory of a vehicle (e.g., an airplane).

Referring now to FIG. 1, a light control system 100 is depicted according to an example embodiment. As shown in FIG. 1, the light control system 100 includes a UV light source 110. When activated, the UV light source 110 can emit UV light 112 to provide a target level of antimicrobial efficacy. For instance, the UV light source 110 can emit the UV light 112 at a predetermined wavelength and intensity for a predetermined exposure time to achieve the target level of antimicrobial efficacy during an activation cycle. In one example, the UV light source 110 can emit the UV light 112 at an intensity of 10 mW/cm$^2$ for an exposure time of 10 seconds to achieve the target level of antimicrobial efficacy for the activation cycle.

Also, as examples, the UV light source 110 can include one or more excimer bulbs, mercury-vapor lamps, down-shifting phosphor lamps, excimer lasers, organic light emitting diodes (OLEDs), and/or light emitting diodes (LEDs). More generally, the UV light source 110 can be a light source that emits the UV light 112 at a wavelength within the UV spectrum (i.e., between approximately 10 nanometers (nm) and approximately 400 nm). In some implementations, the UV light source 110 can be a light source that emits UV light 112 at a wavelength within the far-UV spectrum (e.g., between approximately 190 nm and approximately 240 nm). For instance, in one implementation, the UV light source 110 can be a light source that emits the UV light 112 at a wavelength of approximately 222 nm. By emitting the UV light 112 at a wavelength in the far-UV spectrum, the UV light source 110 can more rapidly disinfect the environment than by emitting the UV light 112 at other wavelengths in the UV spectrum.

As shown in FIG. 1, the light control system 100 also includes a power converter 114 coupled to the UV light source 110. The power converter 114 receives an input power from a power source 116 at an input 118 and outputs a supply power to the UV light 112 source at an output 120. As an example, the power source 116 can provide the input power as an alternating-current (AC) power. In one implementation, the power source 116 can provide the input power as a three-phase AC power with a voltage of 115 volts (V) and a frequency of 400 Hertz (Hz). For instance, in a vehicle, the power source 116 can include an engine turbine that generates electrical energy and an electrical distribution system that provides the generated electrical energy to the light control system 100 in the form of the input power. Other example power sources 116 are also possible.

The power converter 114 converts the input power into the supply power. Within examples, the supply power can have a different AC waveform than the input power. For instance, the supply power can have a different frequency, voltage, and/or current than the input power. More generally, the supply power can have a wattage that is greater than a wattage of the input power. As such, the power converter 114 can provide the UV light source 110 with the supply power, which is sufficient to emit the UV light 112 at the target level of antimicrobial efficacy. In one example, the input power can have a wattage that is less than 1 kW and the supply power can have a wattage that is equal to or greater than 1 kW.

In FIG. 1, the power converter 114 includes the input 118, a rectifier 122, a direct current (DC) link 124, an inverter 126, a power buffer 128, and the output 120. The rectifier 122 is coupled to and receives the input power from the input 118. The rectifier 122 can convert the AC input power into a DC power. In an example, the rectifier 122 includes a power factor corrector (PFC) 130 that corrects a power factor of the input power to facilitate more efficient use of the input power by the light control system 100. The PFC 130 can also facilitate isolating the light control system 100 from the power source 116 (and/or other electrical subsystems coupled to the power source 116). Within examples, the PFC 130 can include a passive PFC circuit, an active PFC circuit, and/or a dynamic PFC circuit.

The rectifier 122 is coupled to the inverter 126 via the DC link 124. As described in further detail below, when the UV light source 110 is activated, the inverter 126 converts the DC power received from the rectifier 122 into an AC power, which provides a portion of the supply power at the output 120. The DC link 124 facilitates the coupling of the rectifier 122 and the inverter 126. In one example, the DC link 124 can include a capacitor coupled in parallel between the rectifier 122 and the inverter 126. The DC link 124 can assist in mitigating transients propagating toward the power source 116 and/or assist in smoothing pulses in the rectified DC power provided by the rectifier 122.

As shown in FIG. 1, the power buffer 128 is coupled in parallel between the rectifier 122 and the DC link 124, and between the DC link 124 and the inverter 126. The power buffer 128 stores power using the input power received at the input 118 when the UV light source 110 deactivated. As examples, the power buffer 128 can include a battery, a capacitor, and/or another type of energy storage device.

In the example of FIG. 1, the power buffer 128 includes a plurality of DC-to-DC converters 132 coupled to each other. When the UV light source 110 is deactivated, the DC-to-DC converters 132 receive the DC power from the rectifier 122. In one implementation, the DC-to-DC converters 132 include a first DC-to-DC converter that steps down the DC power received from the rectifier 122 and a second DC-to-DC converter that steps up the DC power. This configuration of the DC-to-DC converters 132 can beneficially reduce (or minimize) the size and/or weight of the power buffer 128.

As noted above, inverter 126 is coupled to the rectifier 122 and the power buffer 128. In this arrangement, when the UV light source 110 is activated, the inverter 126 can receive the DC power from the rectifier 122 and the power stored in the power buffer 128. The inverter 126 can convert this combination of DC power from the rectifier 122 and the power buffer 128 into the supply power, which has an AC waveform. In an example, the inverter 126 can include a pulse-width modulator (PWM) 134, which can switch on and off to control a frequency of the supply power. In another example, the inverter 126 can additionally or alternatively include a sine wave generator and/or a carrier wave generator to convert the combination of DC power to the supply power.

As further shown in FIG. 1, the light control system 100 can also include a control device 136 communicatively coupled to the power converter 114, a light sensor 138, and one or more trigger sensors 140. In general, the control device 136 can (i) communicate with the light sensor 138 and/or the trigger sensor(s) 140 to receive information related to the operation of the light control system 100 and/or (ii) communicate with the power converter 114 to control operation of the light control system 100 based on the information received from the light sensor 138 and/or the trigger sensor(s) 140. As described in further detail below, the control device 136 can additionally or alternatively be incorporated in the light sensor 138, the trigger sensor(s) 140, and/or other components of the light control system 100.

In some examples, the control device 136 can control the operation of the light control system 100 by activating the UV light source 110. For instance, in one example, the trigger sensor(s) 140 can detect one or more trigger conditions and responsively generate a trigger-sensor signal indicating that the trigger condition(s) were detected. The control device 136 can (i) receive the trigger-sensor signal indicating that the trigger condition was detected, (ii) determine, based on the trigger-sensor signal, that one or more criteria are met, and (iii) responsive to the determination that the one or more criteria are met, transmit a control signal to activate the UV light source 110.

As examples, the trigger sensor(s) 140 can include a motion sensor, an occupancy sensor, a thermal sensor, a door open/close sensor, an infrared sensor device, an ultrasonic sensor device, a floor pressure sensor, and/or other types of sensors. For instance, in an example in which the light control system 100 is located on a vehicle having a lavatory, the trigger condition(s) detected by the trigger sensor(s) 140 can include a door of the lavatory being opened, the door of the lavatory being closed, the lavatory being occupied, and/or the lavatory being unoccupied. Additionally, for example, the one or more criteria that is used by the control device 136 to determine whether to activate the UV light source 110 can include one or more criterion such as a door of the lavatory being closed, the lavatory being unoccupied, the lavatory having been occupied a predetermined number of times since a previous activation of the UV light source 110, and/or a predetermined amount of time having passed since the previous activation of the UV light source 110.

In an additional or alternative example, the trigger sensor(s) 140 can be configured to sense a parameter related to the operation of one or more component of the power converter 114. For instance, the trigger sensor(s) 140 can include a sensor for measuring the amount of power stored in the power buffer 128. In such example, the trigger sensor(s) 140 can generate the trigger-sensor signal to indicate the amount of power is stored in the power buffer 128, and the control device 136 can determine whether the indicated amount of power is sufficient to activate the UV light source 110 at the target level of antimicrobial efficacy during an activation cycle. For instance, the control device 136 can compare the amount of power indicated by the trigger-sensor signal to a threshold amount of power stored in the control device 136. Responsive to the control device 136 determining that the indicated amount of power is greater than the threshold amount of power, the control device 136 can transmit the control signal to the power converter 114 to activate the UV light source 110. Whereas, responsive to the control device 136 determining that the indicated amount of power is less than the threshold amount of power, the control device 136 can continue to wait until the power buffer 128 has stored at least the threshold amount of power before transmitting the control signal.

In an additional or alternative example, the trigger sensor(s) 140 can include a user input device that is actuatable by an operator. As examples, the user input device can include one or more buttons, mice, keypads, keyboards, and/or switches. Responsive to the operator actuating the user input device, the user input device can transmit the trigger-sensor signal to the control device 136 to cause the control device 136 to transmit the control signal to the power converter 114 for activating the UV light source 110. In this way, the trigger sensor(s) 140 can provide for on-demand actuation of the light control system 100 to disinfect a given environment (e.g., a hospital room and/or an aircraft lavatory).

In some examples, the control device 136 can additionally or alternatively control the operation of the light control system 100 by deactivating the UV light source 110. For instance, the control device 136 can deactivate the UV light source 110 to prevent (or delay) a future activation cycle and/or to terminate a current activation cycle (i.e., to override a decision, based on a trigger-sensor signal, to activate the UV light source 110).

Within examples, the control device 136 can deactivate the UV light source 110 responsive to an occurrence of one or more override conditions to enhance (or maximize) operational safety and/or reduce (or minimize) operational transients. In general, the override conditions can include, for example, conditions relating to one or more components of the light control system 100 (e.g., a temperature of a component of the light control system 100 and/or an amount of energy stored in the power buffer 128) and/or conditions relating to an environment in which the component(s) of the light control system 100 are located (e.g., a temperature of the environment and/or an occupancy of the environment).

As further examples, the override conditions can additionally or alternatively include conditions relating to (i) an occurrence of an emergency state of one or more devices external to the light control system 100 (e.g., an emergency state of one or more devices on an aircraft and/or in a hospital), and/or (ii) an occurrence of an attempt to tamper with one or more components of the light control system 100.

In one implementation, the trigger sensor(s) 140 can detect the override condition(s) and responsively generate an override-sensor signal indicating that the override condition(s) were detected. The control device 136 can (i) receive the override-sensor signal indicating that the override condition(s) were detected, (ii) determine, based on the override-sensor signal, that one or more criteria are met, and (iii) responsive to the determination that the one or more criteria are met, transmit a control signal to deactivate the UV light source 110.

In one example, the trigger sensor(s) 140 can detect when a door opens or a person enters a vicinity of the light control system 100, and the control device 136 can responsively cause the light control system 100 to deactivate as a security and/or safety feature. Additionally, for instance, when the door subsequently closes and/or the person subsequently leaves the vicinity of the light control system 100, the trigger sensor 140 can transmit the trigger-sensor signal to the control device 136 to activate the light control system 100 and/or prepare the light control system 100 to be activated responsive to a next trigger-sensor signal from the trigger sensor(s) 140.

In another example, the trigger sensor(s) 140 can detect when a temperature of the UV light source 110 and/or an environment in which the UV light source 110 is located is greater than a threshold temperature level. The threshold temperature level can be related to, for instance, an overheating condition and/or an out-of-tolerance temperature condition. Responsive to the trigger sensor(s) 140 detecting that the temperature is greater than the threshold temperature level, the control device 136 can deactivate the light control system 100 to reduce (or minimize) a risk of an operational transient in the light control system 100. Additionally, when the trigger sensor(s) 140 detect that the temperature of the UV light source 110 and/or the environment returns to an in-tolerance temperature (e.g., a temperature less than the threshold temperature level), the trigger sensor(s) 140 can transmit the trigger-sensor signal to the control device 136 to activate the light control system 100 and/or prepare the light control system 100 to be activated responsive to a next trigger-sensor signal from the trigger sensor(s) 140.

In some examples, the control device 136 can transmit the control signal to the power converter 114 to deactivate the UV light source 110. For instance, in one implementation, the control device 136 can transmit the control signal to one or more switches 142A-142C to actuate the switch(es) 142A-142C from a closed state to an open state to deactivate the component(s) of the light control system 100 downstream of the switch(es) 142A-142C. In the closed state, each switch 142A-142C can conduct power through the switch 142A-142C. Whereas, in the open state, each switch 142A-142C can inhibit or prevent power transmission through the switch 142A-142C (e.g., actuate the switches 142A-142C to prevent the UV light source 110 from receiving the supply power).

In FIG. 1, for instance, the switches 142A-142C include a first switch 142A located at any point between the input 118 and the rectifier 122, a second switch 142B located at any point between the rectifier 122 and the power buffer 128, and a third switch 142C located at any point between the inverter 126 and the UV light source 110 (e.g., the output 120). In this arrangement, the control device 136 can selectively transmit the control signal to one or more of the switches 142A-142C to specifically deactivate the components of the light control system 100 downstream of those switches 142A-142C. This can allow the control device 136 to selectively deactivate different portions of the light control system 100 based on the specific override condition detected.

For instance, as one example, in a situation in which an override condition occurs with respect to the UV light source 110, it can be beneficial to allow the power buffer 128 to continue to store power (e.g., charge up) while the override condition is resolved for the UV light source 110. This can beneficially allow for more rapid activation of the UV light source 110 using the power stored in the power buffer 128 when the override condition is resolved. In FIG. 1, the control device 136 can transmit the control signal to the third switch 142C to actuate the third switch 142C to the open state while the first switch 142A and the second switch 142B remain in the closed state. As such, the power buffer 128 can continue to receive power from the rectifier 122 while the output 120 and the UV light source 110 are disconnected from the inverter 126 (and, thus, deactivated).

As another example, in a situation in which the trigger sensor(s) 140 detect an occurrence of an override condition with respect to the power buffer 128 (e.g., an out-of-tolerance temperature condition), the control device 136 can deactivate the power buffer 128 (e.g., by transmitting the control signal to the actuate the second switch 142B to the open state) while allowing power to continue to be supplied to other components of the light control system 100 (e.g., by maintaining the first switch 142A and the third switch 142C in the closed state). In practice, for instance, the trigger sensor(s) 140 can detect when a temperature of the power buffer 128 and/or an environment in which the power buffer 128 is located is greater than a threshold temperature level (e.g., indicating an occurrence of an out-of-tolerance temperature condition and/or an overheating condition). Responsive to the trigger sensor(s) 140 detecting that the temperature is greater than the threshold temperature level, the control device 136 can deactivate the power buffer 128 to reduce (or minimize) a risk of an operational transient in the light control system 100. Additionally, when the trigger sensor(s) 140 detect that the temperature of the power buffer 128 and/or the environment returns to an in-tolerance temperature (e.g., a temperature less than the threshold temperature level), the trigger sensor(s) 140 can transmit the trigger-sensor signal to the control device 136 to activate the power buffer 128 and resume storing power in the power buffer 128.

Although three switches 142A-142C are depicted in FIG. 1, the light control system 100 can include a lesser quantity and/or a greater quantity of switches 142A-142C at additional or alternative locations within the light control system 100 in other example embodiments. For instance, in another example, the switch(es) 142A-142C can be additionally or alternatively provided in the rectifier 122, in the inverter 126, in the power buffer 128, at a point before the input 118, at a point after the output 120, and/or any other point between the power source 116 and the output 120. This can beneficially allow for greater options of deactivating the select components of the light control system 100. Specifically, the trigger sensor(s) 140 and the control device 136 can operate in a similar manner to that described above to selectively deactivate the rectifier 122, the PFC 130, the inverter 126, and/or the PWM 134 responsive to detecting an occurrence of an override condition in connection with the component(s) to be deactivated.

In some examples, the combination of the trigger sensor(s) 140 and the control device 136 can additionally or alternatively operate together to monitor the amount of power stored in the power buffer 128, and determine that the amount of power stored in the power buffer 128 is greater than a threshold amount of power. Responsive to the control device 136 determining that the amount of power stored in the power buffer 128 is greater than the threshold amount of power, the control device 136 can deactivate the power buffer 128 to inhibit supplying additional power to the power buffer 128. Later, when the control device 136 determines that the amount of power stored in the power buffer 128 is less than the threshold amount of power, the control device 136 can transmit another control signal to activate the power buffer 128. This can facilitate discontinuing supplying power to the power buffer 128 after the power buffer 128 is fully charged, and then recharging the power buffer 128 after an activation cycle is completed. Additionally or alternatively, deactivating and activating the power buffer 128 can facilitate stopping and/or slowing down a rate of power storage to reduce the likelihood (or avoid) overpowering the UV light source 110 (e.g., providing more power than is needed by the UV light source 110).

In the examples described above, the light control system 100 can operate to selectively activate and/or deactivate one or more components of the light control system 100. As noted above, the light control system 100 can additionally or alternatively operate in connection with the power converter 114, the light sensor 138, and/or the trigger sensor(s) 140 to dynamically adjust an electrical parameter of the supply power provided by the power converter 114 to the UV light source 110. Specifically, the light sensor 138 and/or the trigger sensor(s) 140 can sense one or more operating conditions that can relate to operation of the UV light source 110 (and/or affect an output of the UV light source 110). For example, as noted above, the operating condition(s) that can affect the intensity of the UV light 112 emitted by the UV light source 110 include, for instance, LLD and/or LDD. As additional examples, the operating condition(s) can relate to a temperature of the UV light source 110, an operating frequency of the UV light source 110, a remaining life expectancy of the UV light source 110, a power efficiency of the UV light source 110, an irradiance of the UV light 112 emitted by the UV light source 110, a voltage level of the UV light source 110, an efficacy level of the UV light source 110, and/or an age of the UV light source 110 (e.g., a remaining life expectancy of the UV light source 110).

As described in detail below, responsive to the light sensor 138 and/or the trigger sensor(s) 140 sensing the operating condition(s), the light sensor 138 and/or the trigger sensor(s) 140 can transmit to the control device 136 a sensor signal indicating an input parameter related to the operating condition sensed by the light sensor 138 and/or the trigger sensor(s) 140. Based on the sensor signal, the control device 136 can provide a feedback signal to the PFC 130, the PWM 134, and/or the power buffer 128 to cause the PFC 130, the PWM 134, and/or the power buffer 128 to adjust the electrical parameter of the supply power (e.g., the frequency, the pulse width, the wattage, and/or the voltage of the AC waveform of the supply power) based on the input parameter. In this way, the light control system 100 can maintain a target level of antimicrobial efficacy over a series of activation cycles and/or otherwise adjust operation of the UV light source 110 based on the operating condition(s).

In some implementations, the control device 136 can provide the feedback signal to the PWM 134 to adjust, based on the input parameter, a pulse width and/or a frequency of the supply power. In other implementations, the control device 136 can additionally or alternatively provide the feedback signal to the PFC 130 to adjust, based on the input parameter, a voltage and/or wattage of the supply power. In other implementations, the control device 136 can additionally or alternatively provide the feedback signal to the power buffer 128 to adjust, based on the input parameter, the voltage and/or the wattage of the supply power. Thus, within examples, the control device 136 can cause any one or a combination of the PFC 130, the PWM 134, and/or the power buffer 128 to adjust the electrical parameter of the supply power based on the input parameter related to the operating conditions sensed by the light sensor 138 and/or the trigger sensor(s) 140.

In some examples, the light sensor 138 can sense the UV light 112 emitted by the UV light source 110, measure an optical parameter of the sensed UV light 112, and provide a sensor signal to the control device 136 indicating the optical parameter measured by the light sensor 138. Accordingly, the light sensor 138 can be positioned such that a portion of the UV light 112 emitted by the UV light source 110 is incident on the light sensor 138. As examples, the light sensor 138 can include one or more photodiodes, photojunction devices, light dependent resistors (LDRs), and/or photoconductive cells to sense and measure the optical parameter of the UV light 112.

In these examples, the optical parameter measured by the light sensor 138 can be the input parameter indicated by the sensor signal. The control device 136 can receive the sensor signal from the light sensor 138, and compare the optical parameter indicated by the sensor signal to a target optical parameter. The target optical parameter can be a fixed value and/or an adjustable value. Based on the comparison, the control device 136 can provide a feedback signal to the power converter 114 to cause the power converter 114 to adjust an electrical parameter of the supply power.

In an example in which the electrical parameter is the frequency and/or the pulse width of the AC waveform of the supply power, the feedback signal can cause the PWM 134 to switch of and off based on the feedback signal to adjust the frequency and/or the pulse-width of the AC waveform of the supply power. In one implementation, the optical parameter measured by the light sensor 138 can be related to a resonance of the power converter 114 relative to the UV light source 110. For instance, when the UV light source 110 is activated using the supply power, a gas in the UV light source 110 can undergo a process of ion formation and ion recombination, which can define a frequency of the UV light source 110. When the AC waveform of the supply power has a frequency and/or pulse width that is resonant with the frequency of the UV light source 110, the intensity of the UV light 112 emitted by the UV light source 110 is at a maximum intensity consistent with the input power received at the input 118.

Within examples, the light sensor 138 can measure the irradiance of the UV light 112 as an indication of the resonance of the power converter 114 relative to the UV light source 110. For instance, based on one or more characteristics of the power converter 114 and/or the UV light source 110, the irradiance of the UV light 112 can be expected to have a target irradiance when the power converter 114 is in resonance with the UV light source 110 (i.e., when the frequency and/or pulse width of the supply power is in resonance with the frequency of the UV light source 110). The control device 136 can thus compare the irradiance indicated by the sensor signal to the target irradiance and, based on the comparison, the control device 136 can provide the feedback signal to the power converter 114 to tune the power converter 114 to the frequency of the UV light source 110. Because the frequency of the UV light source 110 may drift over time, the control device 136 and the light sensor 138 can dynamically adjust operation of the power converter 114 to maintain the power converter 114 in resonance with the UV light source 110 over a plurality of activation cycles of the UV light source 110 (e.g., over the life of the UV light source 110).

Further, by tuning the power converter 114 to the frequency of the UV light source 110, the efficiency of the UV light source 110 can be increased (or maximized). In turn, this can allow for the power buffer 128 to be relatively smaller and/or lighter as less power may need to be stored in the power buffer 128 to meet the power requirements of the UV light source 110 for emitting the UV light 112 at the target level of antimicrobial efficacy.

As noted above, the target optical parameter can be a fixed value in one example. In an alternative example, the target optical parameter can be adjustable. For instance, the control device 136 can iteratively adjust the target optical parameter using one or more previously measured optical parameters to maintain the measured irradiance at a peak value.

Figure 2:
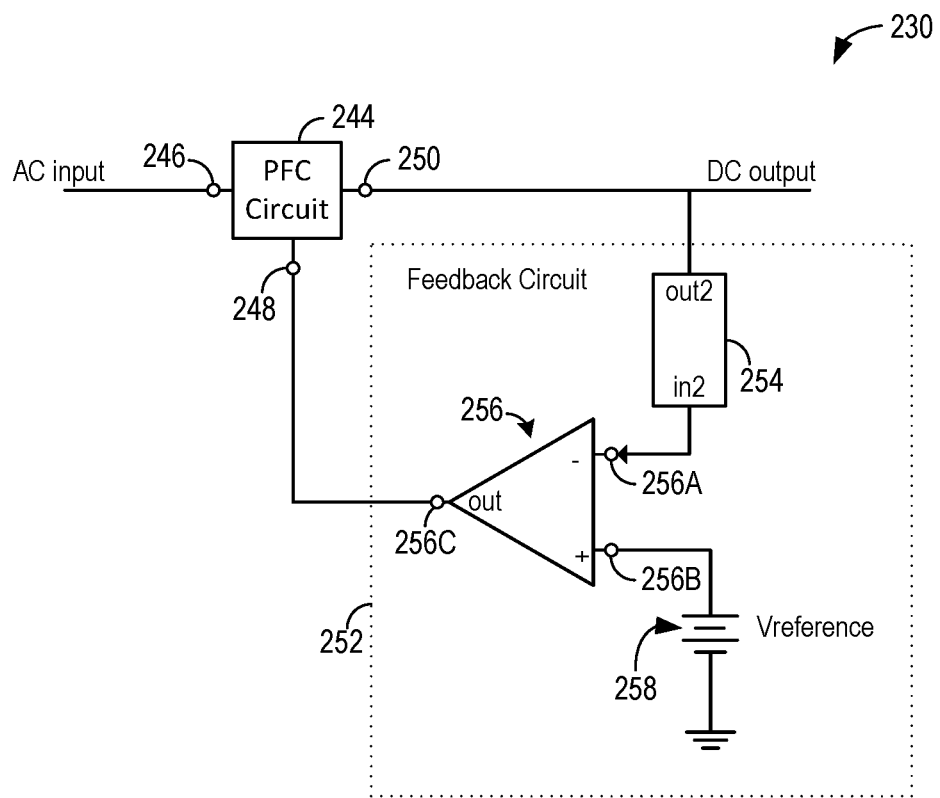
FIG. 2 illustrates a circuit diagram of a power factor corrector according to an example embodiment.

In one implementation in which the PWM 134 adjusts the electrical parameter, the PFC 130 can provide a fixed DC power to the inverter 126. FIG. 2 depicts a PFC 230 according to one example embodiment in which the PFC 230 provides a fixed DC power to the inverter 126. As shown in FIG. 2, the PFC 230 includes a PFC circuit 244 having a first PFC input 246, a second PFC input 248, and a PFC output 250. The first PFC input 246 is configured to receive, via the input 118, the input power from the power source 116. The second PFC input 248 is configured receive a signal from a feedback circuit 252. The PFC output 250 is configured to output a DC power, which is based on the input power at the first PFC input 246 and the signal at the second PFC input 248. As such, the PFC output 250 can be coupled to the power buffer 128 and/or the inverter 126 in FIG. 1.

The feedback circuit 252 is coupled to the PFC output 250 and the second PFC input 248. In this arrangement, the signal that the feedback circuit 252 provides to the second PFC input 248 is based on the DC power at the PFC output 250. As such, the feedback circuit 252 can sense variations in the DC power at the PFC output 250 and provide the signal to the second PFC input 248 that indicate the sensed variations. The PFC circuit 244 can thus use the signal at the second PFC input 248 as a basis for converting the input power to the DC power with a fixed voltage (i.e., correcting the power factor and/or regulating the voltage of the DC power at the PFC output 250).

In FIG. 2, the feedback circuit 252 includes a signal conditioning circuit 254, an operational amplifier (op-amp) 256, and a reference voltage source 258. The signal conditioning circuit 254 is coupled to the PFC output 250 and an inverting input 256A of the op-amp 256, the reference voltage source 258 is coupled to a non-inverting input 256B of the op-amp 256, and an output 256C of the op-amp 256 is coupled to the second PFC input 248. In this arrangement, the op-amp 256 is configured to output to the second PFC input 248 the signal, which is based on a difference between a voltage provided by the signal conditioning circuit 254 at the inverting input 256A and a voltage of the reference voltage source 258 at the non-inverting input 256B. As the voltage of the reference voltage source 258 is a fixed value, the feedback circuit 252 is configured to cause the PFC circuit 244 to maintain the DC power at the PFC output 250 at a single, fixed voltage.

In the examples described above, the electrical parameter of the supply power that is adjusted is the frequency and/or the pulse width of the AC waveform of the supply power. As noted above, however, the electrical parameter of the supply power that is adjusted can additionally or alternatively be a voltage and/or a wattage of the supply power in other examples. In such examples, the control device 136 can provide the feedback signal to the PFC 130 and/or the power buffer 128 to adjust the voltage and/or the wattage of the supply power.

Figure 3:
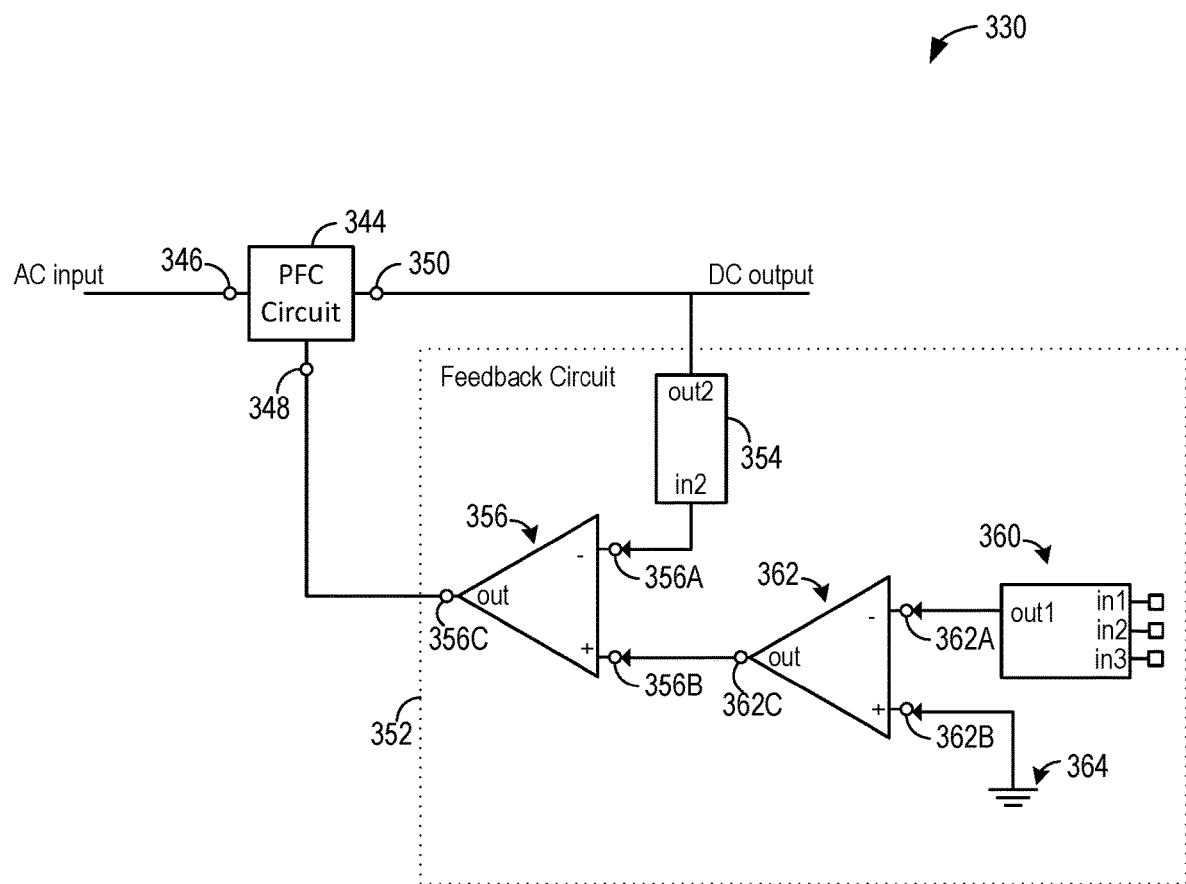
FIG. 3 illustrates a circuit diagram of a power factor corrector according to another example embodiment.

FIG. 3 depicts a PFC 330 that can adjust, based on the feedback signal, the voltage of the DC power provided to the inverter 126 and/or the power buffer 128 in FIG. 1, according to an example embodiment. In FIG. 3, the PFC 330 is a modified version of the PFC 230 depicted in FIG. 2, wherein the reference voltage source 258 that causes the PFC 230 to provide a single, fixed voltage at the PFC output 250 in FIG. 2 has been replaced by components that facilitate dynamically selecting a reference voltage from among a plurality of reference voltages and, thus, adjusting the voltage of the DC power provided to the inverter 126 and/or the power buffer 128. For instance, as described below, the PFC 330 can include an operational amplifier (op-amp) having a variable input as a reference voltage.

As shown in FIG. 3, the PFC 330 includes a PFC circuit 344 having a first PFC input 346, a second PFC input 348, and a PFC output 350. The first PFC input 346 is configured to receive, via the input 118, the input power from the power source 116. The second PFC input 348 is configured receive a signal from a feedback circuit 352. The PFC output 350 is configured to output a DC power, which is based on the input power at the first PFC input 346 and the signal at the second PFC input 348. As such, the PFC output 350 can be coupled to the power buffer 128 and/or the inverter 126 in FIG. 1.

The feedback circuit 352 is coupled to the PFC output 350 and the second PFC input 348. In this arrangement, the signal that the feedback circuit 352 provides to the second PFC input 348 is based on the DC power at the PFC output 350. As such, the feedback circuit 352 can sense variations in the DC power at the PFC output 350 and provide the signal to the second PFC input 348 based, in part, on the sensed variations. This can allow the PFC circuit 334 to use the signal at the second PFC input 348 as a basis for converting the input power at the first PFC input 346 to a regulated, power-factor corrected DC power at the PFC output 350.

Additionally, the feedback circuit 352 is configured to provide the signal at the second PFC input 348 based on the input parameter related to the operating condition(s) that are sensible by the light sensor 138 and/or the trigger sensor(s) 140. As the input parameter can vary with changes in the operating condition(s), the signal at the second PFC input 348 can also allow the PFC circuit 344 to dynamically adjust the voltage level of the DC power at the PFC output 350 responsive to the changes in the operating condition(s). Stated differently, the PFC 330 can dynamically adjust the voltage of the DC power by outputting a regulated, power-factor corrected voltage level selected from among a plurality of regulated, power-factor corrected voltage levels based on the input parameter.

As noted above, the signal at the second PFC input 348 is based, in part, on the input parameter related to the operating condition(s) sensed by the light sensor 138 and/or the trigger sensor(s) 140. This can be achieved based on the control device 136 communicatively coupled to the PFC 130 as shown in FIG. 1. For instance, the control device 136 can (i) receive, from the light sensor 138 and/or the trigger sensor(s) 140, the sensor signal indicating the input parameter related to the operating condition sensed by the light sensor 138 and/or the trigger sensor(s) 140, and (ii) based on sensor signal, provide the feedback signal to the PFC 330 to cause the PFC 330 to adjust, based on the input parameter, the electrical parameter of the supply power.

Specifically, in FIG. 3, the feedback circuit 352 can include a logic circuit 360, which receives the feedback signal from the control device 136. The logic circuit 360 is configured to select a reference voltage from among a plurality of reference voltages based on the input parameter. For instance, in one implementation, the logic circuit 360 can include a variable voltage divider having an output voltage, which is dynamically adjustable based on the input parameter. In FIG. 3, the logic circuit 360 is depicted as being configured to select among three reference voltages based on the input parameter. However, in other examples, the logic circuit 360 can be configured to select among N different reference voltages based on the input parameter, where N is an integer value that is greater than one.

As shown in FIG. 3, the feedback circuit 352 includes a first op-amp 356, a second op-amp 362, and the logic circuit 360. The first op-amp includes a first inverting input 356A, a first non-inverting input 356B, and a first output 356C. The first output 356C of the first op-amp 356 is coupled to the second PFC input 348. The first inverting input 356A of the first op-amp 356 is coupled to the PFC output 350 by a signal conditioning circuit 354. The second op-amp 362 includes a second inverting input 362A, a second non-inverting input 362B, and a second output 362C. The second output 362C of the second op-amp 362 is coupled to the first non-inverting input 356B of the first op-amp 356. The second inverting input 362A of the second op-amp 362 is coupled to a ground 364. The logic circuit 360 is coupled to the second inverting input 362A of the second op-amp 362. The logic circuit 360 is thus configured to provide the adjustable reference voltage to the second inverting input 362A of the second op-amp 362.

In this arrangement, the logic circuit 360 can receive the feedback signal from the control device 136 and select, based on the input parameter, the reference voltage from among the plurality of reference voltages. The logic circuit 360 can provide the selected reference voltage to the second inverting input 362A of the second op-amp 362. The second op-amp 362 then outputs, from the second output 362C to the first non-inverting input 356B of the first op-amp 356, a signal based on a difference between the selected reference voltage at the second inverting input 362A and the ground 364 at the second non-inverting input 362B. The first op-amp 356 then outputs, from the first output 356C to the second PFC input 348, a signal based on a difference between the signal received from the second op-amp and a signal received from the signal conditioning circuit 354 (which is based on the DC power at the PFC output 350).

The signal provided by the feedback circuit 352 at the second PFC input 348 is thus based on the feedback signal received by the PFC 330 from the control device 136 and the input parameter sensed by the light sensor 138 and/or the trigger sensor(s) 140. Accordingly, because the DC power at the PFC output 350 is based on the input power at the first PFC input 346 and the signal at the second PFC input 348, the PFC 330 can dynamically adjust the voltage of the DC power to be at a regulated, power-corrected level (which is selected from among a plurality of regulated, power-factor corrected voltage levels) based on the input parameter. In this way, the PFC 330 is configured to adjustably control the electrical parameter of the supply power.

As noted above, the operating condition(s) can relate to a temperature of the light source, an operating frequency of the light source, a remaining life expectancy of the light source, a power efficiency of the light source, an irradiance of light emitted by the light source, a voltage level of the light source 110, an efficacy level of the light source 110, and/or an age of the light source 110. Thus, when one or more of these operating condition(s) change over time and/or a series of activation cycles, the light sensor 138 and/or the trigger sensor(s) 140 can sense the changes and the control device 136 can responsively cause the PFC 130 to adjust the voltage of the DC power provided to the inverter 126 and thereby adjust the voltage of the supply power provided to the UV light source 110. This can, for example, facilitate the UV light source 110 emitting the UV light 112 at a target intensity that provides a target level of antimicrobial efficacy over time and/or the series of activation cycles. Additionally, for example, adjusting the voltage of the supply power based on changed operating condition(s) can facilitate extending the useful life of the UV light source 110.

Figure 4:
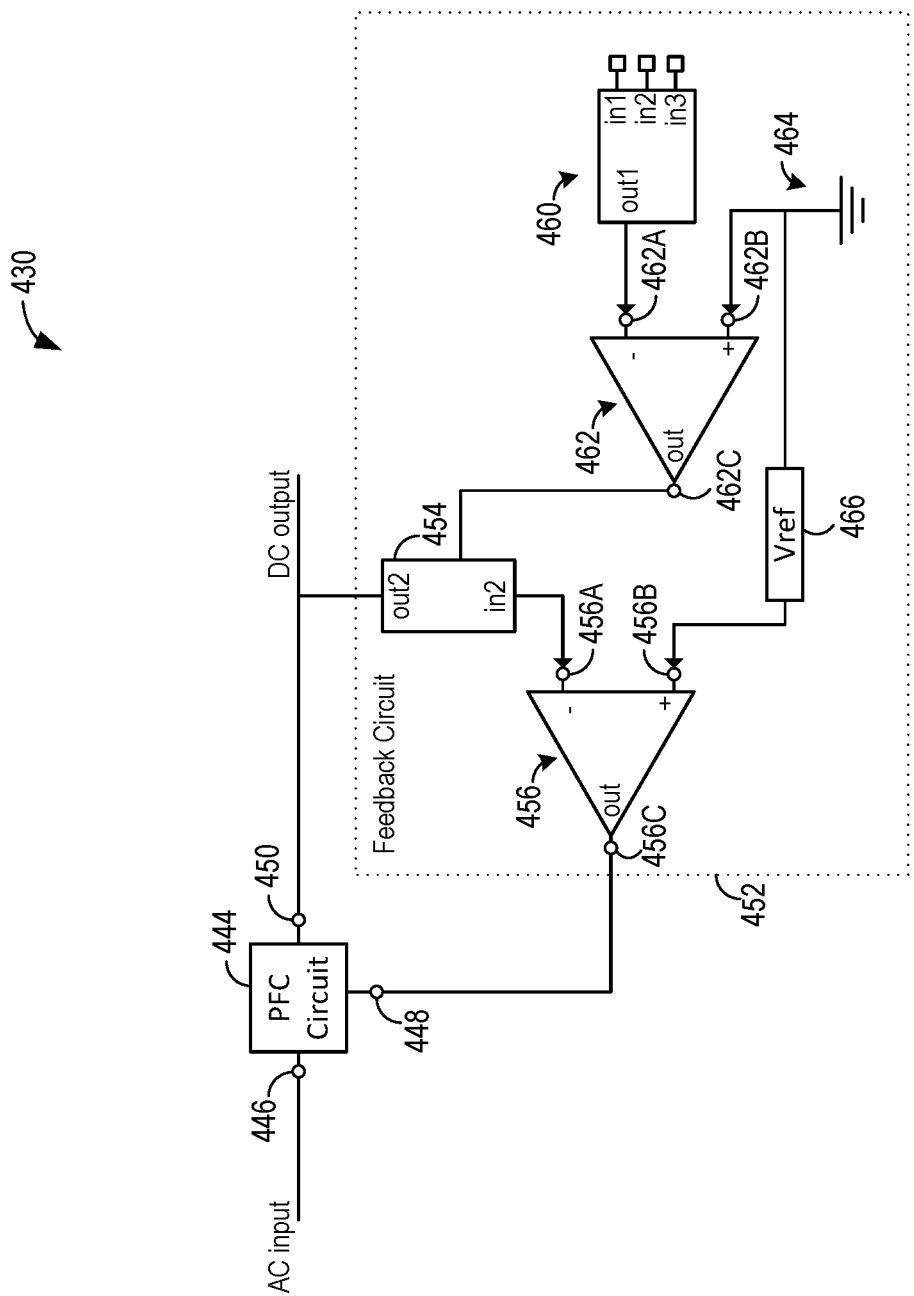
FIG. 4 illustrates a circuit diagram of a power factor corrector according to another example embodiment.

Referring now to FIG. 4, a PFC 430 that can adjust, based on the feedback signal, the voltage of the supply power is illustrated according to another example embodiment. As shown in FIG. 4, the PFC 430 includes a PFC circuit 444 having a first PFC input 446, a second PFC input 448, and a PFC output 450. The first PFC input 446 is configured to receive, via the input 118, the input power from the power source 116. The second PFC input 448 is configured receive a signal from a feedback circuit 452. The PFC output 450 is configured to output the DC power, which is based on the input power at the first PFC input 446 and the signal at the second PFC input 448. The feedback circuit 452 is coupled to the PFC output 450 and the second PFC input 448.

Like the feedback circuit 352 in FIG. 3, the feedback circuit 452 is configured to receive the feedback signal from the control device 136 and provide the signal to the second PFC input 448 to dynamically adjust the voltage of the DC power to be at a regulated, power-corrected level (which is selected from among a plurality of regulated, power-factor corrected voltage levels) based on the input parameter. However, the feedback circuit 452 shown in FIG. 4 differs in some ways from the feedback circuit 352 shown in FIG. 3.

As shown in FIG. 3, the feedback circuit 352 includes a first op-amp 356, a second op-amp 362, and the logic circuit 360. The first op-amp includes a first inverting input 356A, a first non-inverting input 356B, and a first output 356C. The first output 356C of the first op-amp 356 is coupled to the second PFC input 348. The first inverting input 356A of the first op-amp 356 is coupled to the PFC output 350 by a signal conditioning circuit 354. The second op-amp 362 includes a second inverting input 362A, a second non-inverting input 362B, and a second output 362C. The second output 362C of the second op-amp 362 is coupled to the first non-inverting input 356B of the first op-amp 356. The second inverting input 362A of the second op-amp 362 is coupled to a ground 364. The logic circuit 360 is coupled to the second inverting input 362A of the second op-amp 362. The logic circuit 360 is thus configured to provide the adjustable reference voltage to the second inverting input 362A of the second op-amp 362.

As shown in FIG. 4, the feedback circuit 452 includes a first op-amp 456, a second op-amp 462, and a logic circuit 460. The first op-amp 456 includes a first inverting input 456A, a first non-inverting input 456B, and a first output 456C. The first output 456C of the first op-amp 456 is coupled to the second PFC input 448, and the first inverting input 456A of the first op-amp 456 is coupled to the PFC output 450 by a signal conditioning circuit 454. The second op-amp 462 includes a second inverting input 462A, a second non-inverting input 462B, and a second output 462C. The second output 462C of the second op-amp 462 is coupled, via the signal conditioning circuit 454, to the PFC output 450 and the first inverting input 456A of the first op-amp 456. The second non-inverting input 462B of the second op-amp 462 is coupled to a ground 464.

Additionally, as shown in FIG. 4, the feedback circuit 452 includes a reference voltage source 466 coupled to the first non-inverting input 456B of the first op-amp 456 and the second non-inverting input 462B of the second op-amp 462. The reference voltage source 466 is configured to provide a fixed voltage to the first non-inverting input 456B and the second non-inverting input 462B. The feedback circuit 452 also includes a logic circuit 460 coupled to the second inverting input 462A of the second op-amp 462. The logic circuit 460 is configured to provide an adjustable reference voltage to the second inverting input 462A of the second op-amp 462. As described above with respect to the logic circuit 360 shown in FIG. 3, the logic circuit 460 is configured to select the reference voltage from among a plurality of reference voltages based on the input parameter.

In this arrangement, the logic circuit 460 can receive the feedback signal from the control device 136 and select, based on the input parameter, the reference voltage from among the plurality of reference voltages. The logic circuit 460 can provide the selected reference voltage to the second inverting input 462A of the second op-amp 462. The second op-amp 462 then outputs, from the second output 462C to the signal conditioning circuit 454, a signal based on a difference between the selected reference voltage at the second inverting input 462A and the ground 464 at the second non-inverting input 462B.

The signal conditioning circuit 454 can provide a signal to the first inverting input 456A of the first op-amp 456 that is based on (i) the DC power at the PFC output 450 and (ii) the signal provided by the second output 462C of the second op-amp 462. Additionally, the reference voltage source 466 can provide the fixed voltage to the first non-inverting input 456B of the first op-amp 456. The first op-amp 456 then outputs, from the first output 456C to the second PFC input 448, a signal based on a difference between the fixed voltage from the reference voltage source 466 and the signal received from the signal conditioning circuit 454 (which is based on the DC power at the PFC output 450 and the reference voltage selected based on the input parameter).

In this way, the signal provided by the feedback circuit 452 at the second PFC input 448 is based on the feedback signal received by the PFC 430 from the control device 136 and the input parameter sensed by the light sensor 138 and/or the trigger sensor(s) 140. Accordingly, because the DC power at the PFC output 450 is based on the input power at the first PFC input 446 and the signal at the second PFC input 448, the PFC 430 can dynamically adjust the voltage of the DC power to be at a regulated, power-corrected level (which is selected from among a plurality of regulated, power-factor corrected voltage levels) based on the input parameter.

In some examples, changing the voltage at the PFC 130 can provide greater flexibility in certain parameters than used by the PWM 134 (e.g., parameters of the PWM 134 such as, for instance, voltage and current de-rating of components in the PWM 134, thermal dissipation of PWM 134 as compared to parameters of the PFC 130 such as, for instance, voltage, interact with frequency and pulse width).

Figure 5:
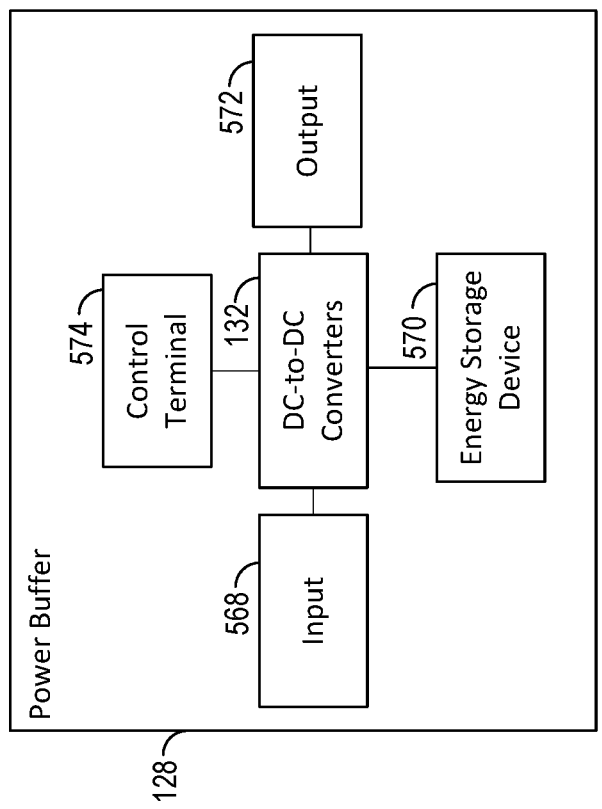
FIG. 5 illustrates a simplified block diagram of a power buffer according to an example embodiment.

As noted above, the control device 136 can additionally or alternatively provide the feedback signal to the power buffer 128 to adjust the voltage and/or the wattage of the supply power. FIG. 5 depicts a simplified block diagram of the power buffer 128 according to an example embodiment. As shown in FIG. 5, the power buffer 128 can include an input 568 configured to receive an electrical power from the PFC 130 during a first portion of a time interval. The power buffer 128 can also include an energy storage device 570 configured to store the electrical power received at the input 568 during the first portion of the time interval. The power buffer 128 can further include an output 572 configured to be coupled to the PWM 134. The output 572 is configured to, during a second portion of the time interval, output the electrical power stored in the energy storage device 570 during the first portion of the time interval.

Also, as shown in FIG. 5, the power buffer 128 includes the DC-to-DC converters 132 that can step down and/or step up the power received at the input 568 and/or the power provided at the output 572. Additionally, the power buffer 128 includes a control terminal 574 configured to receive, from the control device 136, the feedback signal for controlling operation of the energy storage device 570. For instance, in one implementation, the feedback signal can cause the DC-to-DC converters 132 to step up and/or step down power stored in the energy storage device 570 and/or drawn from the energy storage device 570 based on the input parameter. In this way, the control device 136 can additionally or alternatively provide the feedback signal to the power buffer 128 to adjust, based on the input parameter sensed by the light sensor 138 and/or the trigger sensor(s) 140, the voltage and/or the wattage of the supply power.

As noted above, the light sensor 138 and/or the trigger sensor(s) 140 can sense the operating condition(s) and provide a sensor signal indicating an input parameter related to the operating condition(s) sensed by the light sensor 138 and/or the trigger sensor(s) 140. Additionally, as noted above, the operating condition(s) and the input parameter(s) can relate to a temperature of the UV light source 110, an operating frequency of the UV light source 110, a remaining life expectancy of the UV light source 110, a power efficiency of the UV light source 110, an irradiance of the UV light 112 emitted by the UV light source 110, a voltage level of the UV light source 110, an efficacy level of the UV light source 110, and/or an age of the UV light source. The operating condition(s) and the input parameter(s) can additionally or alternatively relate to an occupancy of an environment in which the UV light source 110 is located by humans and/or babies, and/or a vicinity of the humans and/or babies to the UV light source 110. The operating condition(s) and the input parameter(s) can additionally or alternatively relate to a level of power that has been stored in the power buffer 128 and/or an occurrence of a maximum level of power being stored in the power buffer 128.

In some examples, the trigger sensor(s) 140 can sense a temperature of the UV light source 110 and responsively adjust, based on the sensed temperature, the electrical parameter of the supply power. Additional details regarding using the temperature to adjust and/or determine the supply power provided to the UV light source 110 are described in U.S. patent application Ser. 15/810,414, filed Nov. 13, 2017, which is hereby incorporated by reference in its entirety.

For example, as described in U.S. patent application Ser. No. 15/810,414, the UV light source 110 can overheat due to operating conditions occurring internal to the UV light source 110 and/or external to the UV light source 110. For instance, during operation of the UV light source 110, filaments and/or columns of conducting plasma of gas can form between dielectrics and electrodes. The filaments can attach at a set location within the UV light source 110 and form voltage discharges, which heat a metal mesh and may form holes and/or cracks in the metal mesh. In this manner, the voltage discharges reduce a lifespan of the UV light source 110.

Within examples, the trigger sensor(s) 140 can include at least one temperature sensor that is configured to monitor the internal temperature of the UV light source 110. Thus, when the filaments create one or more hot spots, which cause temperature spikes along a metal mesh of the UV light source 110, the temperature sensor can measure the hot spots. In some implementations, the temperature spikes may reach a temperature over approximately 100 degrees Celsius, which can affect the metal mesh and/or the UV light source 110. Based on the temperature sensed by the trigger sensor(s) 140, the control device 136 can cause the PFC 130, the PWM 134, and/or the power buffer 128 to adjust the electrical parameter of the supply power and thereby reduce electrical power supplied to the UV light source 110. The adjustment or reduction of the electrical power shifts the filament with respect to the dielectrics within the UV light source 110. The shift of the filament adjusts a position of the hot spot, thereby extending the lifespan of the UV light source 110.

In another example, the trigger sensor(s) 140 can monitor a temperature external to the UV light source 110 (e.g., in an environment in which the UV light source 110 is located). In one implementation, to maintain a desired functioning of the UV light source 110, the temperature of the load surrounding measured at a certain distance and/or within certain time intervals can be maintained within a predetermined range of temperature values. The trigger sensor(s) 140 can thus indicate the measured temperature to the control device 136, and the control device 136 can compare the measured temperature to the predetermined range of temperature values. If the control device 136 determines that the temperature sensed by the trigger sensor(s) 140 is outside of the predetermined range of temperature values, the control device 136 can determine that the UV light source 110 is underperforming. Additionally, the control device 136 can cause the PFC 130, the PWM 134, and/or the power buffer 128 to adjust the electrical parameter of the supply power and thereby reduce electrical power supplied to the UV light source 110 to increase the wattage of the supply power provided to the UV light source 110.

In general, the control device 136 is a computing device that is configured to control operation of the light control system 100 (and, as described below, a power converter 614 shown in FIG. 6). As such, the control device 136 can be implemented using hardware, software, and/or firmware. For example, the control device 136 can include one or more processors and a non-transitory computer readable medium (e.g., volatile and/or non-volatile memory) that stores machine language instructions or other executable instructions. The instructions, when executed by the one or more processors, cause the light control system 100 to carry out the various operations described herein. The control device 136, thus, can receive data (including data indicated by the sensor signals, trigger-sensor signals, and/or override signals) and store the data in memory as well.

Within examples, the control device 136 can be integrated with one or more of the components of the light control system 100. For instance, aspects of the control device 136 described herein can be incorporated in and/or performed by the control device 136 can be integrated with the PFC 130, the PWM 134, the power buffer 128, the UV light source 110, the light sensor 138, and/or the trigger sensor(s) 140. Accordingly, principles and advantages of distributed processing, such as redundancy, replication, and the like, also can be implemented, as desired, to increase the robustness and performance of the devices and systems of the control device 136.

For instance, in one example, the control device 136 can be the PFC 130. In another example, the control device 136 can be the PWM 134. In another example, the control device 136 can be the power buffer 128. In another example, the control device 136 can be the UV light source 110. In another example, the control device 136 can be the light sensor 138. In another example, the control device 136 can be the trigger sensor(s) 140. As described above, in another example, the control device 136 can be a combination of two or more of the PFC 130, the PWM 134, the power buffer 128, the UV light source 110, the light sensor 138, and the trigger sensor(s) 140. In yet another example, the control device 136 can be a distinct device that is separate from the PFC 130, the PWM 134, the power buffer 128, the UV light source 110, the light sensor 138, and the trigger sensor(s) 140. Accordingly, within examples, the PFC 130, the PWM 134, the power buffer 128, the UV light source 110, the light sensor 138, and/or the trigger sensor(s) 140 can perform some or all of the functions and operations described above for the control device 136.

Additionally, for example, although FIG. 1 depicts the components of the light control system 100 as indirectly communicating with each other via the control device 136, the components of the light control system 100 can directly communicate with each other in implementations in which the control device 136 is integrated in the components of the light control system 100. For instance, aspects of the control device 136 can be integrated in the light sensor 138 and/or the trigger sensor(s) 140 such that the light sensor 138 and/or the trigger sensor(s) 140 can directly communicate the feedback signal and input parameter to the PFC 130, the PWM 134, and/or the power buffer 128. Also, for instance, aspects of the control device 136 can be integrated in the light sensor 138 and/or the trigger sensor(s) 140 such that the light sensor 138 and/or the trigger sensor(s) 140 can activate and/or deactivate components of the light control system 100, as described above. Similarly, within examples, the light sensor 138 and/or the trigger sensor 140 can be integrated with other components of the light control system 100 such as, for instance, the UV light source 110 and/or the power buffer 128.

In the examples described above, the light control system 100 includes the power buffer 128. The power buffer 128 can be beneficial in limited-power environments, including aircraft and non-aircraft implementations of the light control system 100. However, in other examples, the light control system 100 can omit the power buffer 128 (e.g., in implementations in which a relatively high voltage is readily available).

In some implementations (such as, e.g., an airplane), the light control system 100 can provide for transmission of a three-phase power. Whereas, in other implementations (e.g., a commercial application such as a hospital), the light control system 100 can provide for transmission a single phase power.

In operation, the light control system 100 receives, at the input 118 of the power converter 114, the input power from the power source 116 during a first portion of a time interval and a second portion of the time interval. The UV light source 110 is deactivated during the first portion of the time interval. The UV light source 110 is activated during the second portion of the time interval. However, the input power received during the second portion of the time interval is insufficient by itself for the UV light source 110 to emit the UV light 112 at the intensity and/or for the exposure time providing the target level of antimicrobial efficacy.

While the UV light source 110 is deactivated during the first portion of the time interval, the rectifier 122 converts the input power to the DC power and the DC power is stored in the power buffer 128. After the first portion of the time interval, the control device 136 can activate the UV light source 110 during the second portion of the time interval. For example, the control device 136 can activate the UV light source 110 responsive to the trigger sensor(s) 140 detecting the trigger condition(s) and the control device 136 determining, based at least in part on the trigger-sensor signal received from the trigger sensor(s) 140, that the criteria for activating the UV light source 110 are met.

During the second portion of the time interval, the power converter 114 outputs the supply power from the output 120 to the UV light source 110. The UV light source 110 can use the supply power during the second portion of the time interval to emit the UV light 112 at the intensity and/or for the exposure time providing the target level of antimicrobial efficacy.

As noted above, the supply power can include a combination of power from (i) the input power received at the input 118 during the second portion of the time interval, and (ii) the power stored in the power buffer 128 during the first portion of the time interval. For instance, when the UV light source 110 is activated during the second portion of the time interval, the rectifier 122 can convert the input power to the DC power and provide the DC power to the inverter 126. Additionally, when the UV light source 110 is activated during the second portion of the time interval, the power buffer 128 can sense a voltage droop and responsively provide the power stored in the power buffer 128 to the inverter 126. The inverter 126 thus receives the DC power from the rectifier 122 and the stored power from the power buffer 128, and converts this combination of power into the supply power. By combining the input power received at the input 118 during the second portion of the time interval and the power stored in the power buffer 128, the power converter 114 can provide the UV light source 110 with a power that is sufficient to activate the UV light source 110 at the target level of antimicrobial efficacy.

In one example, the target level of antimicrobial efficacy can be defined by an intensity of 10 mW/cm$^2$ intensity and an exposure time of 10 seconds. In this example, the input 118 can receives the input power as a three-phase AC power with a voltage of approximately 115 $V_{AC}$, a frequency of approximately 400 Hz, and a current of 0.5 Amps (A) such that the input power has a wattage of approximately 100 W (i.e., less than 1 kW). As such, the input power is insufficient by itself to activate the UV light source 110 at the target level of antimicrobial efficacy. The rectifier 122 can convert the input power to the DC power having a voltage of approximately 200 $V_{DC}$ and a current of approximately 0.5 A. The power buffer 128 can include a first DC-to-DC converter that steps down the DC power from 200 $V_{DC}$ to 28 $V_{DC}$, and a second DC-to-DC converter that steps the DC power from 28 $V_{DC}$ to 200 $V_{DC}$.

In this arrangement, during the first portion of the time interval, the rectifier 122 converts the input power to the 200 $V_{DC}$ power and the power buffer 128 stores the 200 $V_{DC}$ power. During the second portion of the time interval, the rectifier 122 converts the input power to the 200 $V_{DC}$ power and provides the 200 $V_{DC}$ power to the inverter 126. Also, during the second portion of the time interval, the power buffer 128 provides the stored power to the inverter 126 with a voltage of approximately 200 $V_{DC}$ and a current of approximately 5 A. As a result, the inverter 126 receives the combination of power at 200 $V_{DC}$ and a current of at least 5 A such that the supply power has a wattage equal to or greater than 1 kW. In this example, the power buffer 128 can have an energy storage capacity at least large enough to provide the stored power at 200 $V_{DC}$ and 5 A for the 10 second exposure time. In this way, the power converter 114 can provide the UV light source 110 with sufficient power to achieve the target level of antimicrobial efficacy during the activation cycle of the UV light source 110.

In the example described above, the target level of antimicrobial efficacy is UV dose of approximately 10 mWs/cm$^2$. In additional or alternative examples, the target level of antimicrobial efficacy can be a UV dose between approximately 2 mWs/cm$^2$ and approximately 500 mWs/cm$^2$. Different microorganisms may have different abilities to withstand exposure to the UV light 112. In some implementations, the target level of antimicrobial efficacy can be based on a target microorganism-kill rate for one or more types of microorganisms that are targeted for disinfection by the light control system 100. As examples, the targeted microorganism-kill rate can be approximately 80%, approximately 90%, approximately 95%, approximately 99%, approximately 99.9%, and/or approximately 99.99% of the one or more target organisms irradiated by the UV dose.

Additionally, in the example described above, the power stored in the power buffer 128 provides approximately 90% of the supply power and the input power received during the second portion of the time interval provides approximately 10% of the supply power. In additional or alternative examples, the input power received during the second portion of time can provide approximately 5% to approximately 95% of the supply power and the power stored in the power buffer 128 can provide the remainder of the supply power.

Additionally, during the time interval, the light sensor 138 and/or the trigger sensor(s) 140 can sense an operating condition related to the operation of the UV light source 110, and provide to the control device 136 a sensor signal indicating an input parameter related to the operating condition. Based on sensor signal, the control device 136 can provide the feedback signal to the power converter 114 to cause the power converter 114 to adjust, based on the input parameter, the electrical parameter of the supply power.

Additionally or alternatively, during the time interval, the light sensor 138 and/or the trigger sensor(s) 140 can sense an override condition, and the control device 136 can responsively provide an override signal to one or more switches 142A-142C to deactivate one more components of the light control system 100.

Figure 7:
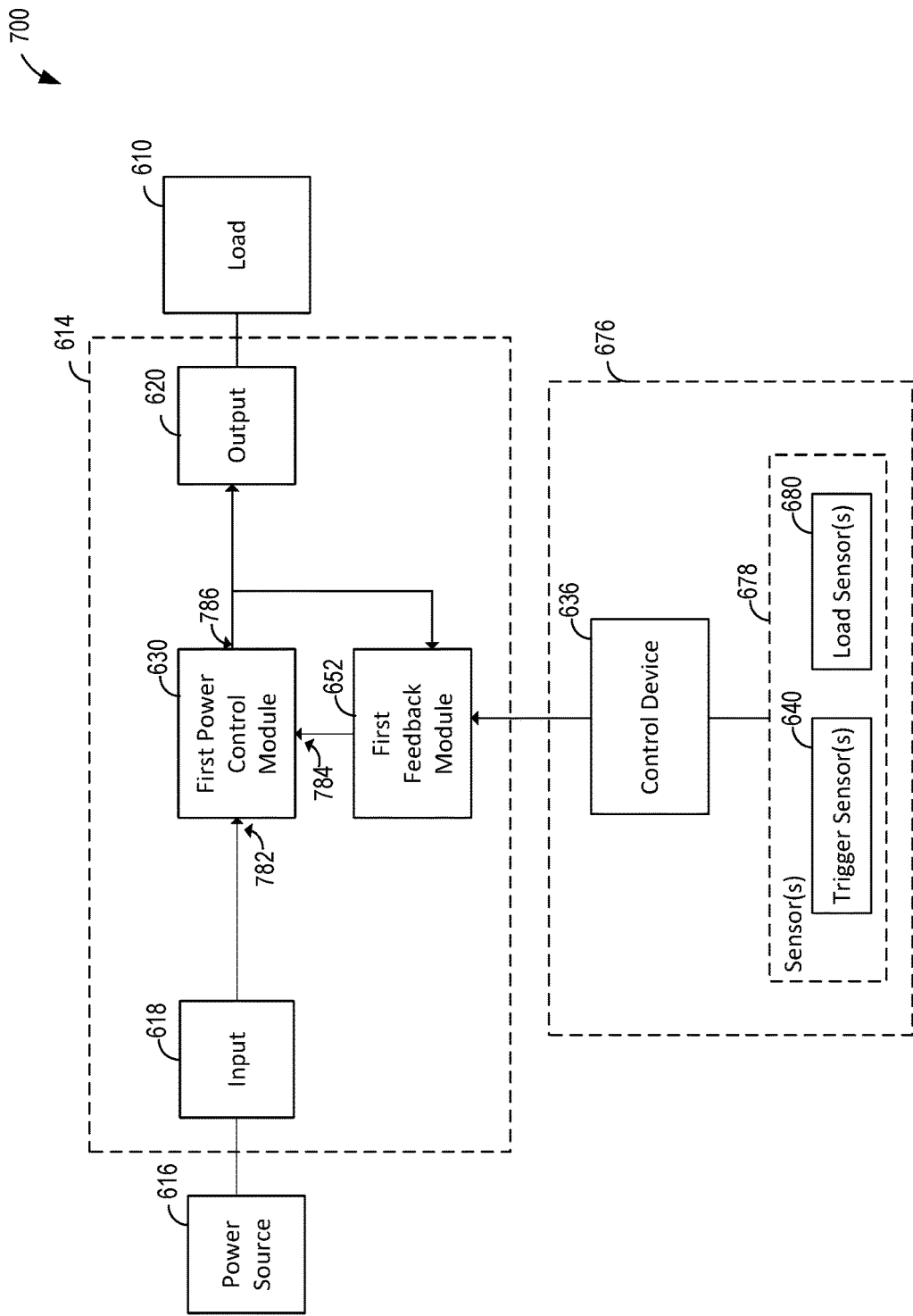
FIG. 7 illustrates a simplified block diagram of a system for supplying power to a load according to another example embodiment.
Figure 8:
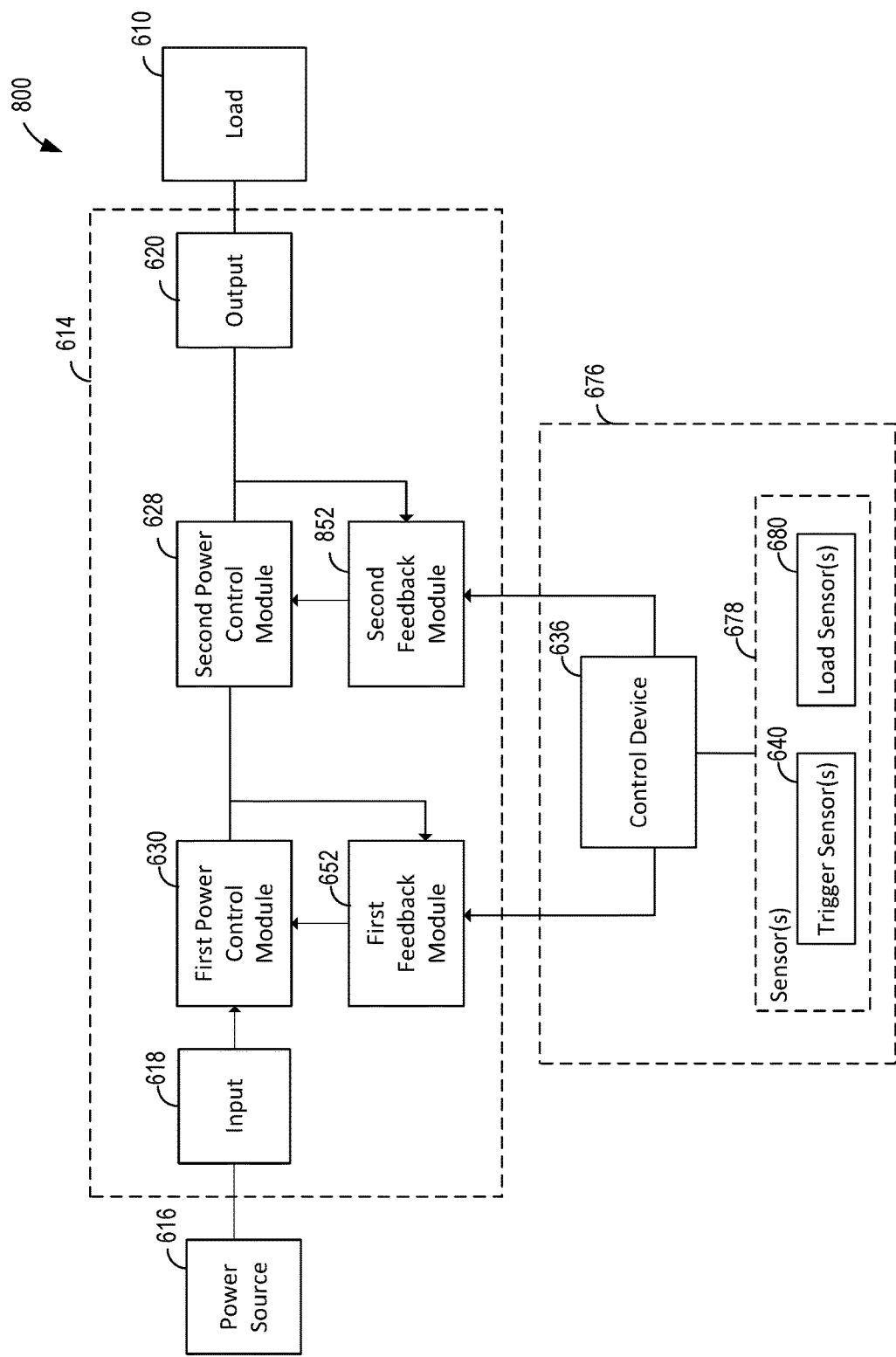
FIG. 8 illustrates a simplified block diagram of a system for supplying power to a load according to another example embodiment.

In the examples described above with respect to FIGS. 1-5, the power converter 114 is a part of a light control system 100 for powering a UV light source 110. However, as noted above, aspects of the light control system 100 can be applied to dynamically adjust a supply power provided to other types of loads. FIGS. 6-8 depict simplified block diagrams of example systems for powering a load according to additional or alternative example embodiments. Within examples, the systems described with respect to FIGS. 6-8 can perform any or all of the functions and/or operations described above with respect to FIGS. 1-5 (e.g., dynamically adjusting a supply power provided to the load, triggering activation or operation of the load, and/or overriding a decision to activate or operate the load).

Figure 6:
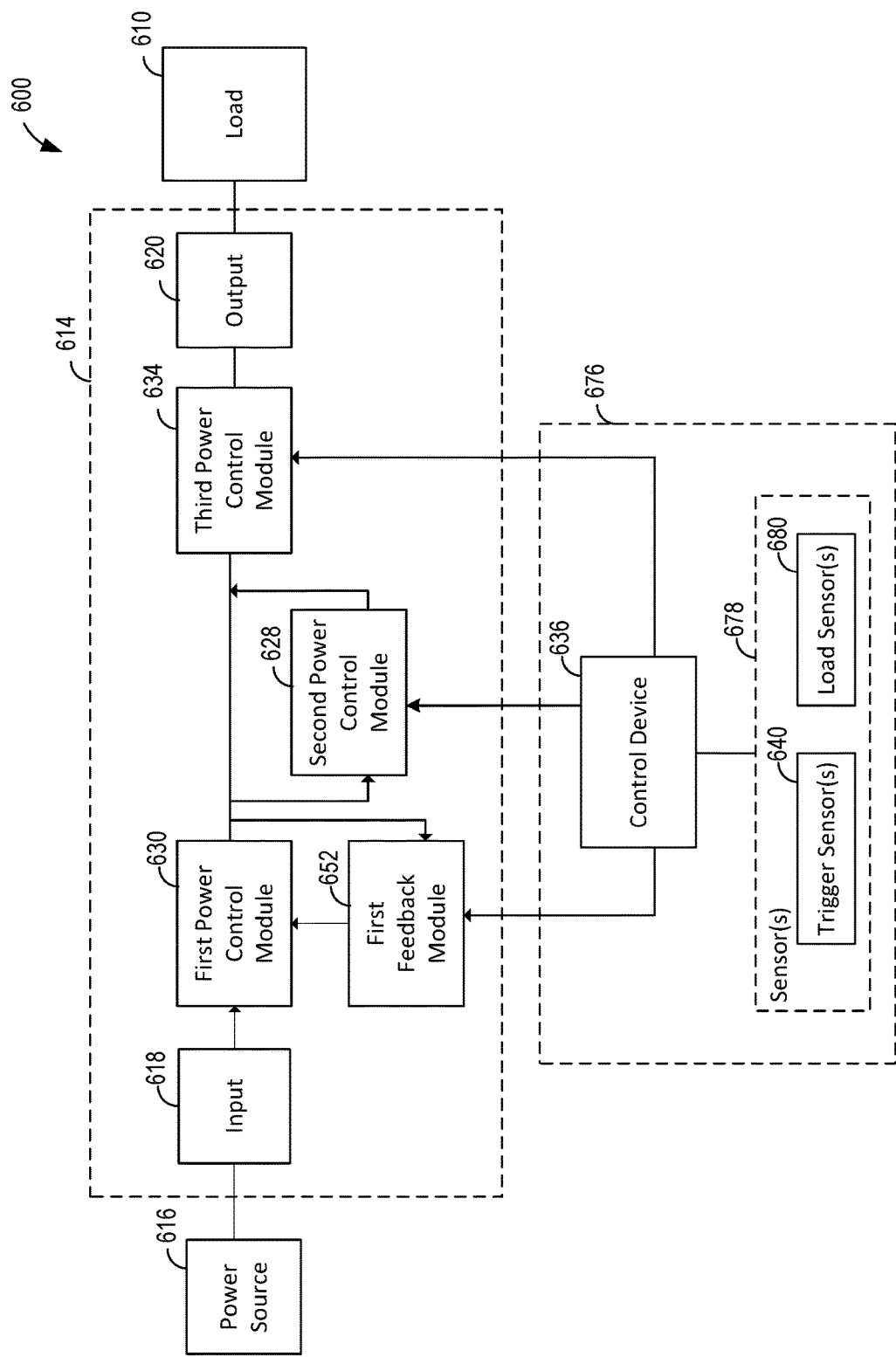
FIG. 6 illustrates a simplified block diagram of a system for supplying power to a load according to another example embodiment.

FIG. 6 depicts a system 600 according to an example embodiment. As shown in FIG. 6, the system 600 includes a power source 616, a power converter 614, a load 610, and a power control system 676. The power source 616 is coupled to and configured to provide an input power to the power converter 614. The power converter 614 is communicatively coupled to the power control system 676. In general, the power control system 676 is configured to provide a plurality of control signals to the power converter 614 to control operations performed by the power converter 614 for converting the input power into a supply power. The power converter 614 is coupled to the load 610, and configured to provide the supply power to the load 610. The load 610 can use the supply power to perform operations. In the examples described above, the load 610 can be a UV light source 110. However, in other examples, the load 610 can additionally or alternatively be a non-UV light source (e.g., a laser), a motor, a travelling wave tube (TWT), a radar device, an electronic thruster (e.g., a thruster that accelerates ions at relativistic velocities to provide thrust), a laser inferometer gauge, a light source that uses a constant non-varying output to emit light, and/or a device that uses a constant non-varying output to generate heat.

More generally, the load 610 can be any load that can benefit from a relatively precise voltage and/or current feed. For instance, in an implementation in which the load 610 includes an electronic thruster, the efficiency of the electronic thruster (and, thus, an ability to keep a satellite in a particular orbit over a useful life of the satellite) can be based, at least in part, on accurate control of the voltage supplied to the electronic thruster over time. Additionally, for instance, in an implementation in which the load 610 includes a laser inferometer gauge, the laser inferometer gauge can be used (e.g., on an airplane) to determine a shim thickness for mating body sections. In such an implementation, relatively precise voltages may beneficially provide for relatively high accuracy of the laser inferometer gauge and assist in dynamically adjusting the power provided to the laser inferometer gauge to help compensate for aging of system components.

The power converter 614 converts the input power into the supply power. Within examples, the supply power can have a different AC waveform than the input power. For instance, the supply power can have a different frequency, voltage, and/or current than the input power. As shown in FIG. 6, the power converter 614 can include an input 618, one or more power control modules 630, 628, 634, and an output 620. The power converter 614 receives an input power from a power source 616 at the input 618 and outputs the supply power to the load 612 source at the output 620.

In general, the power control modules 630, 628, 634 can operate, based on control signals from the power control system 676, to adjust one or more electrical parameters of the power transmitted through the power converter 614. For instance, in FIG. 6, the power control modules 630, 628, 634 include a first power control module 630, a second power control module 628, and a third power control module 634.

The first power control module 630 can receive the input power from the input 618 and output a first adjustable power to the second power control module 628 and/or the third power control module 634. The second power control module 628 can receive the first adjustable power from the first power control module 630 and output a second adjustable power to the third power control module 634. The third power control module 634 can receive the first adjustable power from the first power control module 630 and the second adjustable power from the second power control module 628, and output a third adjustable power to the output 620.

In this example, the supply power provided to the load 610 is the third adjustable power; however, in other examples that may omit the third power control module 634, the supply power can include the first adjustable power, the second adjustable power, or a combination of the first adjustable power and the second adjustable power.

Also, as shown in FIG. 6, a first feedback module 652 can receive an indication of the first adjustable power outputted by the first power control module 630 and provide to the first power control module 630 a signal that is based on (i) the indication of the first adjustable power and (ii) a first control signal received from the control device 636. For instance, the first power control module 630 and the first feedback module 652 can form a PFC such as, for instance, the PFCs 330, 430 that included a feedback circuit 352, 452. As examples, the second power control module 628 can include a power buffer (e.g., the power buffer 128), and the third power control module 634 can include a PWM (e.g., the PWM 134). However, in other examples, any one or a combination of the power control modules 630, 628, 634 can include a PFC, a PWM, and/or a power buffer.

The power control system 676 can include a control device 636, and one or more sensors 678. The sensor(s) 678 can include, for instance, one or more trigger sensors 640 (e.g., the trigger sensors 140) and/or one or more light sensors 138 (or, more generally, load sensors 680 that directly measure an operational output of the load 610). As such, the sensor(s) 678 can sense a condition (e.g., a trigger condition, an override condition, and/or an operating condition) relating to the load and/or an environment in which the load is located. Additionally, the sensor(s) 678 can provide a signal to the control device 636 to indicate a parameter relating to the sensed condition. The control device 636 can receive the signal from the sensor(s) 678 and determine, based on the parameter, whether to trigger the system 600, deactivate the system 600, and/or adjust an electrical parameter of the first adjustable power, the second adjustable power, and/or the third adjustable power. For instance, as described above, the control device 636 can perform a comparison of the parameter and one or more threshold values, and determine whether to perform the above actions based on the comparison. Additionally or alternatively, the control device 636 can automatically make a determination to perform some or all of the actions responsive to the control device 636 receiving a signal from the sensor(s) 678.

Although the control device 636 is depicted as a part of the power control system 676, the control device 636 can additionally or alternatively be integrated with the first power control module 630, the second power control module 628, the third power control module 634, the trigger sensor(s) 640, the load sensor(s) 680, and/or the load 610 in example embodiments (i.e., as described above with respect to the control device 136 in FIGS. 1-5). Thus, as described above, the components of the system 600 can directly and/or indirectly communicate with each other within examples.

Responsive to control device 636 determining that an action is to be taken based on the signal from the sensor(s) 678, the control device 636 can provide further signals to the power converter to trigger the system 600, deactivate the system 600, and/or adjust an electrical parameter of the first adjustable power, the second adjustable power, and/or the third adjustable power. For example, the control device 636 can provide the first control signal to the first feedback module 652 to adjust the electrical parameter of the first adjustable power outputted by the first power control module 630. For instance, the first feedback module 652 can include a logic circuit (e.g., the logic circuit 360 or the logic circuit 460), which receives the first control signal and selects a reference voltage from among a plurality of reference voltages based on the first control signal, as described above. The first feedback module 652 can also include a plurality of op-amps as described above with respect to FIGS. 3-4.

Additionally, for example, the control device 636 can provide a second control signal to the second power control module 628. Based on the second control signal, the second power control module 628 can adjust the electrical parameter of the second adjustable power. Similarly, for example, the control device 636 can provide a third control signal to the third power control module 634. Based on the third control signal, the third power control module 634 can adjust the electrical parameter of the third adjustable power.

In this arrangement, the power control system 676 can selectively transmit the first control signal, the second control signal, and/or the third control signal at the same time or at different times during operation of the system 600 to achieve one or more adjustments to the supply power provided to the load 610. This can beneficially allow for relatively greater control over the supply power and/or allow for finely tuned adjustments to the operation of the load 610 based on the conditions sensed by the sensor(s) 678.

For instance, at a first time, the control device 636 can transmit the first control signal to the first feedback module 652 to adjust the electrical parameter of the first adjustable power. At a second time, the control device 636 can transmit the second control signal to the second power control module 628 to adjust the electrical parameter of the second adjustable power. At a third time, the control device 636 can transmit the third control signal to the third power control module 634 to adjust the electrical parameter of the third adjustable power. At a fourth time, the control device 636 can transmit the first control signal to the first feedback module 652 to adjust the electrical parameter of the first adjustable power and transmit the second control signal to the second power control module 628 to adjust the electrical parameter of the second adjustable power. At a fifth time, the control device 636 can transmit the second control signal to the second power control module 628 to adjust the electrical parameter of the second adjustable power and transmit the third control signal to the third power control module 634 to adjust the electrical parameter of the third adjustable power. At a sixth time, the control device 636 can transmit the first control signal to the first feedback module 652 to adjust the electrical parameter of the first adjustable power, transmit the second control signal to the second power control module 628 to adjust the electrical parameter of the second adjustable power, and transmit the third control signal to the third power control module 634 to adjust the electrical parameter of the third adjustable power.

As noted above, the power converter 614 can include one or more of the first power control module 630, the second power control module 628, and the third power control module 634. Accordingly, in some examples, the power converter 614 can include the first power control module 630 and the first feedback module 652, and omit the second power control module 628 and/or the third power control module 634. In other examples, the power converter 614 can include the second power control module 628 and omit the first power control module 630 (and the first feedback module 652) and/or the third power control module 634. In other examples, the power converter 614 can include the third power control module 634 and omit the first power control module 630 (and the first feedback module 652) and/or the second power control module 628.

Also, in other examples, the power converter 614 can include a feedback module communicatively coupled to the third power control module 634 in a manner similar to the coupling of the first power control module 630 and the first feedback module 652, and the feedback control module coupled to the third power control module 634 can receive the control signal from the control device 636. In such examples, the feedback module can receive an indication of the third adjustable power outputted by the third power control module 634 and provide to the third power control module 634 a signal that is based on (i) the indication of the third adjustable power and (ii) the control signal received from the control device 636.

FIG. 7 depicts a system 700 according to another example embodiment. As shown in FIG. 7, the system 700 is substantially similar to the system 600 shown in FIG. 6, except the system 700 omits the second power control module 628 and the third power control module 634. In this example, the first power control module 630 provides the first adjustable power as the supply power to the output 620.

Additionally, as shown in FIG. 7, the first power control module 630 can include a first input 782 configured to receive the input power from the power source 616, a second input 784 configured to receive the signal from the first feedback module 652, and an output 786 configured to output the supply power, which is based on the input power at the first input 782 and the signal at the second input 784. As noted above, the first feedback module 652 is coupled to the output 786 and the second input 784, and the first feedback module 652 is configured to provide the signal at the second input 784 based on the input parameter related to the condition that is sensible by a sensor(s) 678. Also, as noted above, the condition that is sensed by the sensor(s) 678 can be related to the operation of the load 610.

In one example, the first power control module 630 can include a PFC coupled to the first input 782, the second input 784, and the output 786. In another example, the first power control module 630 can additionally or alternatively include a power buffer coupled to the first input 782, the second input 784, and the output 786. In another example, the first power control module 630 can additionally or alternatively include a PWM coupled to the first input 782, the second input 784, and the output 786. Also, in some examples, the first power control module 630 can be integrated with the first feedback module 652.

FIG. 8 depicts a system 800 according to another example embodiment. As shown in FIG. 8, the system 800 is substantially similar to the system 600 shown in FIG. 6, except the system 800 omits the third power control module 634. Additionally, in FIG. 8, the power converter 614 further includes an optional second feedback module 852 coupled to the output of the second power control module 628 and in communication with the control device 636. In this arrangement, the second feedback module 852 can receive an indication of the second adjustable power outputted by the second power control module 628 and provide to the second power control module 6228 a signal that is based on (i) the indication of the second adjustable power and (ii) the second control signal received from the control device 636.

In general, the feedback control module(s) can provide the systems of the present disclosure with accurate and precise control of the electrical parameter(s) to assist the power control module(s) (e.g., the PFC 130, the PWM 134, and/or the power buffer 128) in providing an output that meets power specifications for operating the load 610 at a desired quality and/or performance level over the life of the load 610 (and also improving the life expectancy of the load 610). For example, the feedback control module(s) can help the power buffer 128 to increase the accuracy and precision of a power buffering capability while providing for safe and secure operation of the system. Additionally, for example, the feedback control module(s) can help the first power control module (such as, e.g., the PFC 130) improve the accuracy and precision of the DC output, which can help to provide an accurate power supplied to the load 610 and, thus, facilitate relatively consistent functioning of the load 610 along with a longer life expectancy. Also, the feedback control module(s) can help the second power control module (such as, e.g., the PWM 134) to improve the accuracy and precision of the power supplied to the load 610, which can help to provide a relatively consistent functioning of the load 610 along with a longer life expectancy.

Figure 9:
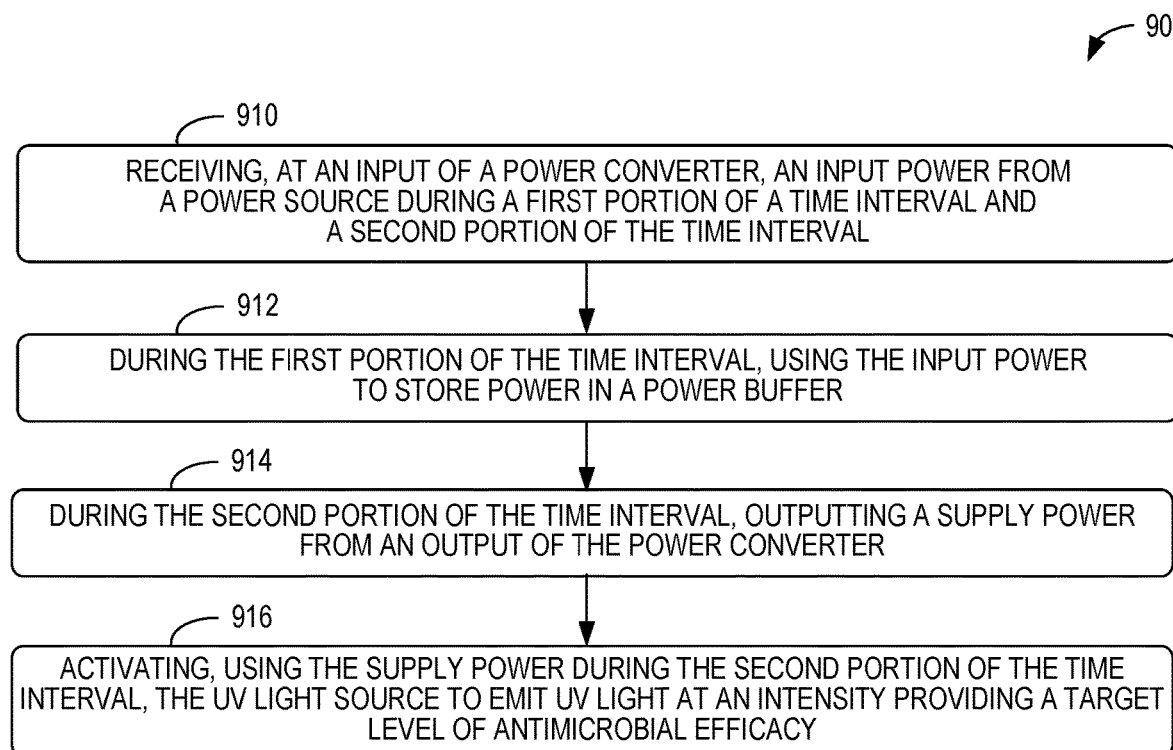
FIG. 9 illustrates a flow chart of an example process for operating a UV light source according to an example embodiment.

Referring now to FIG. 9, a flowchart for a process 900 of operating a UV light source is illustrated according to an example embodiment. As shown in FIG. 9, at block 910, the process 900 includes receiving, at an input of a power converter, an input power from a power source during a first portion of a time interval and a second portion of the time interval. At block 912, during the first portion of the time interval, the process 900 includes using the input power to store power in a power buffer. At block 914, during the second portion of the time interval, the process 900 includes outputting a supply power from an output of the power converter. The supply power includes a combination of power from (i) the input power received at the input during the second portion of the time interval and (ii) the power stored in the power buffer during the first portion of the time interval. At block 916, the process 900 includes activating, using the supply power during the second portion of the time interval, the UV light source to emit UV light at an intensity providing a target level of antimicrobial efficacy. For the process 900, the input power received during the second portion of the time interval is insufficient by itself for activating the UV light source to emit the UV light at the intensity providing the target level of antimicrobial efficacy.

Figure 10:
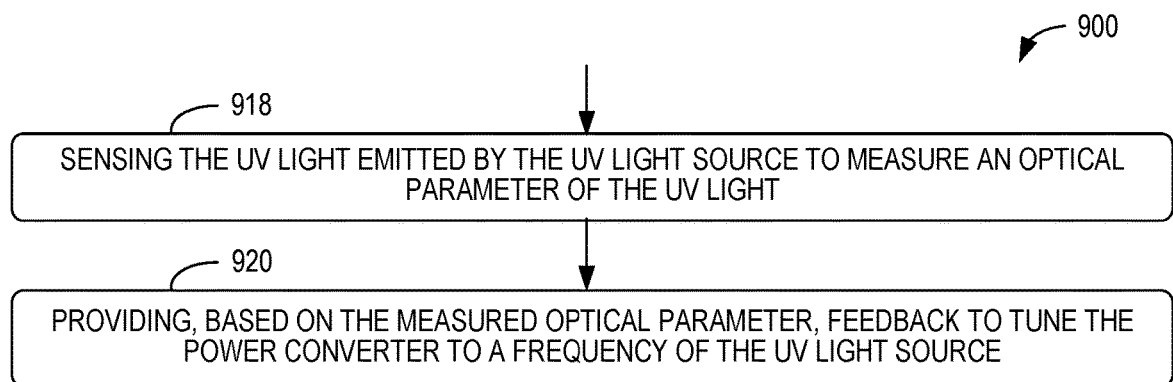
FIG. 10 illustrates a flow chart of an example process for operating a UV light source that can be used with the process shown in FIG. 9.

FIGS. 10-15 depict additional aspects of the process according to further examples. As shown in FIG. 10, the process 900 can further include sensing the UV light emitted by the UV light source to measure an optical parameter of the UV light at block 918. In an example, the optical parameter can be related to a resonance of a power converter relative to the UV light source. At block 920, the process 900 can include providing, based on the measured optical parameter, feedback to tune the power converter to a frequency of the UV light source.

Figure 11:
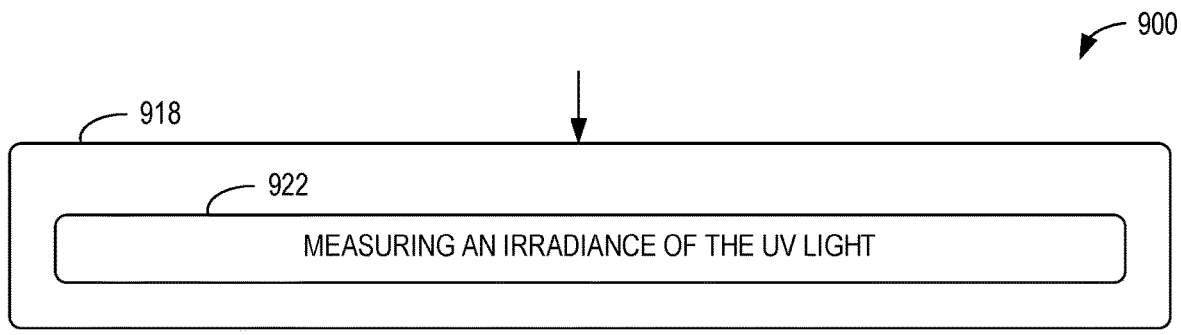
FIG. 11 illustrates a flow chart of an example process for operating a UV light source that can be used with the process shown in FIG. 10.
Figure 12:
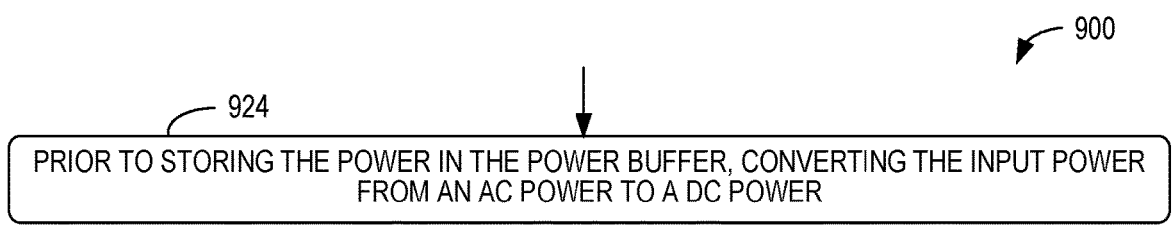
FIG. 12 illustrates a flow chart of an example process for operating a UV light source that can be used with the process shown in FIGS. 9-11.
Figure 13:
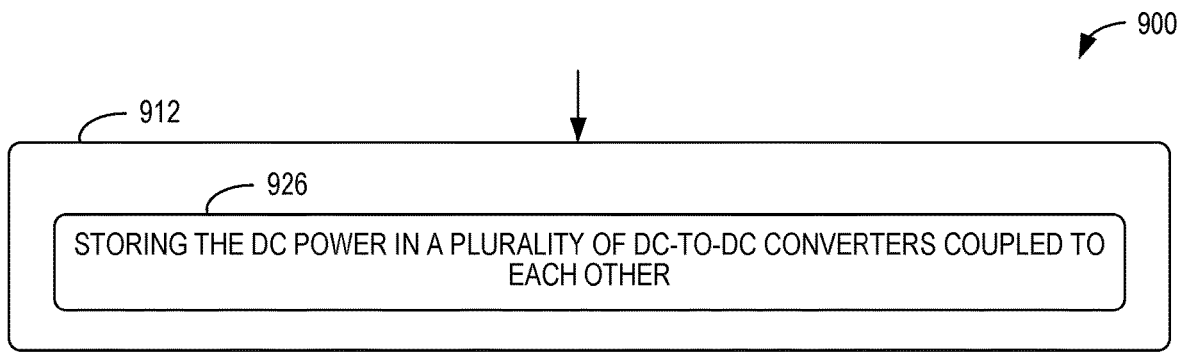
FIG. 13 illustrates a flow chart of an example process for operating a UV light source that can be used with the process shown in FIG. 12.
Figure 14:
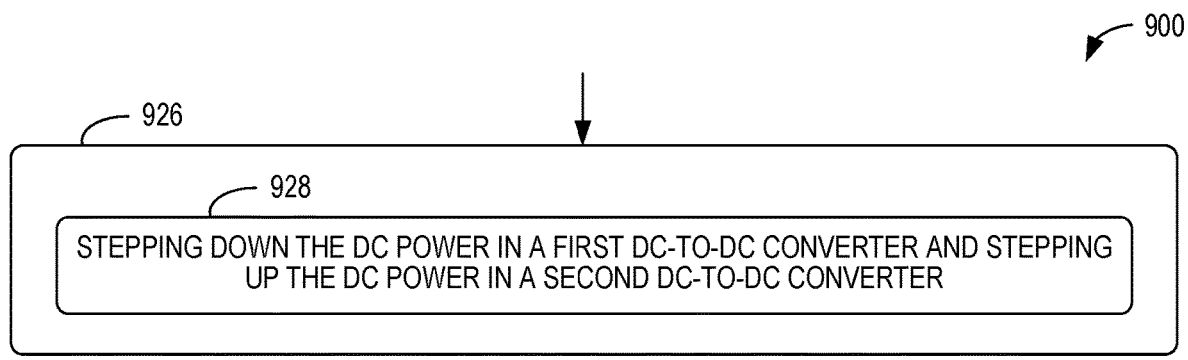
FIG. 14 illustrates a flow chart of an example process for operating a UV light source that can be used with the process shown in FIG. 13.
Figure 15:
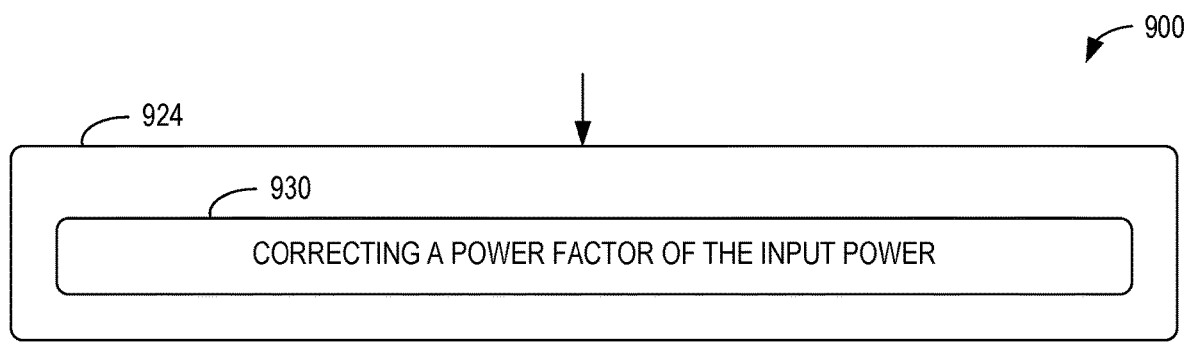
FIG. 15 illustrates a flow chart of an example process for operating a UV light source that can be used with the process shown in FIGS. 12-14.

As shown in FIG. 11, sensing the UV light to measure the optical parameter at block 918 can include measuring an irradiance of the UV light at block 922. As shown in FIG. 12, the process 900 can include, prior to storing the power in the power buffer, converting the input power from an AC power to a DC power at block 924. As shown in FIG. 13, storing the power in the power buffer at block 912 can include storing the DC power in a plurality of DC-to-DC converters coupled to each other at block 926. As shown in FIG. 14, storing the DC power in the plurality of DC-to-DC converters at block 926 can include stepping down the DC power in a first DC-to-DC converter and stepping up the DC power in a second DC-to-DC converter at block 928. As shown in FIG. 15, converting the input power at block 924 can include correcting a power factor of the input power at block 930.

The process 900 can be a linear and/or a non-linear process. Any of the blocks shown in FIGS. 9-14 may represent a module, a segment, or a portion of program code, which includes one or more instructions executable by a processor for implementing specific logical functions or steps in the process. The program code may be stored on any type of computer readable medium or data storage, for example, such as a storage device including a disk or hard drive. Further, the program code can be encoded on a computer-readable storage media in a machine-readable format, or on other non-transitory media or articles of manufacture. The computer readable medium may include non-transitory computer readable medium or memory, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a tangible computer readable storage medium, for example.

In some instances, components of the devices and/or systems described herein may be configured to perform the functions such that the components are actually configured and structured (with hardware and/or software) to enable such performance. Example configurations then include one or more processors executing instructions to cause the system to perform the functions. Similarly, components of the devices and/or systems may be configured so as to be arranged or adapted to, capable of, or suited for performing the functions, such as when operated in a specific manner.

The description of the different advantageous arrangements has been presented for purposes of illustration and description, and is not intended to be exhaustive or limited to the embodiments in the form disclosed. Many modifications and variations will be apparent to those of ordinary skill in the art. Further, different advantageous embodiments may describe different advantages as compared to other advantageous embodiments. The embodiment or embodiments selected are chosen and described in order to explain the principles of the embodiments, the practical application, and to enable others of ordinary skill in the art to understand the disclosure for various embodiments with various modifications as are suited to the particular use contemplated.

Within examples described above, the light control system 100 includes a UV light source, which emits UV light when activated. In additional or alternative examples, the light control system 100 can include a light source that can emit light in other frequency bands. For instance, within examples, the light control system 100 can include a light source that can emit light, which can be used for purposes of disinfection, sanitization or killing germs, microbes, fungus, viruses, to a specified or non-specified target level.

More generally, the present disclosure provides for powering any light source (UV or non-UV) that requires high voltage power source to operate within a desired quality or requirement level in environments in which a high voltage power source is not available. For instance, as described above, the system can include the power buffer mechanism to overcome the shortage of high voltage power source.

Additionally, as described above, feedback and/or control mechanisms are described to facilitate efficient operation of the power buffer, and/or facilitate supplying sufficient power to the light source. The proposed feedback and/or control mechanisms can also provide for operating the light source within a desired range over time, under varying conditions, and/or when given varying parameters through time.

What is claimed is:

1. A power factor corrector (PFC), comprising:
   a first PFC input configured to receive an input power from a power source;
   a second PFC input configured to receive a signal from a feedback circuit; and
   a PFC output configured to output a direct current (DC) power, which is based on the input power at the first PFC input and the signal at the second PFC input,
   wherein the feedback circuit has an output electrically coupled to the second PFC input and is configured to output the feedback signal responsive to a signal received at a first input to the feedback circuit from the PFC output and an input parameter received at a second input to the feedback circuit, wherein the input parameter controls a logic circuit of the feedback circuit to output one of a plurality of reference voltages for controlling an amount of voltage delivered via the PFC output, and
   wherein the input parameter is related to a condition that is sensible by a sensor, and wherein the condition is related to operation of a load.

2. The PFC of claim 1, wherein the load is a light source, and
   wherein the condition is related to at least one of a temperature of the light source, an operating frequency of the light source, a remaining life expectancy of the light source, a power efficiency of the light source, an irradiance of light emitted by the light source, a voltage level of the light source, an efficacy level of the light source, or an age of the light source.

3. The PFC of claim 1, wherein the PFC output is coupled to at least one of a power buffer or a pulse-width modulator (PWM).

4. The PFC of claim 1, wherein the feedback circuit comprises:
   a first operational amplifier (op-amp) including a first inverting input, a first non-inverting input, and a first output, wherein the first output of the first op-amp is coupled to the second PFC input, wherein the first inverting input of the first op-amp is coupled to the PFC output;
   a second op-amp including a second inverting input, a second non-inverting input, and a second output, wherein the second output of the second op-amp is coupled to the first non-inverting input of the first op-amp, wherein the second inverting input of the second op-amp is coupled to a ground; and
   wherein the logic circuit is electrically coupled to the second non-inverting input of the second op-amp to output one of the plurality of reference voltages to the second non-inverting input.

5. The PFC of claim 4, wherein the logic circuit comprises a variable voltage divider having an output voltage, which is based on the input parameter.

6. The PFC of claim 1, wherein the feedback circuit comprises:
   a first op-amp including a first inverting input, a first non-inverting input, and a first output, wherein the first output of the first op-amp is coupled to the second PFC input, wherein the first inverting input of the first op-amp is coupled to the PFC output;
   a second op-amp including a second inverting input, a second non-inverting input, and a second output, wherein the second output of the second op-amp is coupled to the PFC output and the first non-inverting input of the first op-amp, wherein the second inverting input of the second op-amp is coupled to a ground;
   a reference voltage source coupled to the first inverting input of the first op-amp and the second inverting input of the second op-amp, wherein the reference voltage source is configured to provide a fixed voltage to the first inverting input and the second inverting input; and
   wherein the logic circuit is electrically coupled to the second non-inverting input of the second op-amp to output one of the plurality of reference voltages to the second non-inverting input.

7. The PFC of claim 6, wherein the logic circuit comprises a variable voltage divider having an output voltage, which is based on the input parameter.

8. A power control module, comprising:
   a first input of the power control module configured to receive an input power from a power source;
   a second input of the power control module configured to receive a feedback signal from a feedback module; and
   an output configured to output to a supply power, which is based on the input power at the first input and the feedback signal at the second input,
   wherein the feedback module has an output electrically coupled to the second input of the power control module and is configured to output the feedback signal responsive to a signal received at a first input to the feedback module from the PFC output and an input parameter received at a second input to the feedback module, wherein the input parameter controls a logic circuit of the feedback module to output one of a plurality of reference voltages for controlling an amount of voltage delivered via the PFC output, and
   wherein the input parameter is related to a condition that is sensible by a sensor, and
   wherein the condition is related to operation of a load.

9. The power control module of claim 8, wherein the condition is related to at least one of a temperature of the load, an operating frequency of the load, a remaining life expectancy of the load, a power efficiency of the load, a voltage level of the load, or an age of the load.

10. The power control module of claim 8, further comprising a power factor corrector (PFC) coupled to the first input, the second input, and the output.

11. The power control module of claim 8, further comprising a pulse-width modulator coupled to the first input, the second input, and the output.

12. The power control module of claim 8, further comprising a power buffer coupled to the first input, the second input, and the output.

13. The power control module of claim 8, wherein the feedback module comprises a feedback circuit, wherein the feedback circuit comprises:

a first operational amplifier (op-amp) including a first inverting input, a first non-inverting input, and a first output, wherein the first output of the first op-amp is coupled to the second input, wherein the first inverting input of the first op-amp is coupled to the output;

a second op-amp including a second inverting input, a second non-inverting input, and a second output, wherein the second output of the second op-amp is coupled to the first non-inverting input of the first op-amp, wherein the second inverting input of the second op-amp is coupled to a ground; and wherein the logic circuit is electrically coupled to the second non-inverting input of the second op-amp to output one of the plurality of reference voltages to the second non-inverting input.

14. The power control module of claim 13, wherein the logic circuit comprises a variable voltage divider having an output voltage, which is based on the input parameter.

15. The power control module of claim 8, wherein the feedback module comprises a feedback circuit, wherein the feedback circuit comprises:
a first op-amp including a first inverting input, a first non-inverting input, and a first output, wherein the first output of the first op-amp is coupled to the second input, wherein the first inverting input of the first op-amp is coupled to the output;
a second op-amp including a second inverting input, a second non-inverting input, and a second output, wherein the second output of the second op-amp is coupled to the output and the first non-inverting input of the first op-amp, wherein the second inverting input of the second op-amp is coupled to a ground;
a reference voltage source coupled to the first inverting input of the first op-amp and the second inverting input of the second op-amp, wherein the reference voltage source is configured to provide a fixed voltage to the first inverting input and the second inverting input; and
wherein the logic circuit is electrically coupled to the second non-inverting input of the second op-amp to output one of the plurality of reference voltages to the second non-inverting input.

16. A power buffer comprising:
an input configured to receive an electrical power from a power factor corrector (PFC) during a first portion of a time interval, wherein the PFC includes a first PFC input configured to receive the electrical power, a second PFC input configured to receive a feedback signal from a feedback circuit, and a PFC output configured to deliver power, wherein the feedback circuit includes an output electrically coupled to the second PFC input and is configured to output the feedback signal responsive to a signal received at a first input to the feedback circuit from the PFS output and an input parameter received at a second input to the feedback circuit, wherein the input parameter controls a logic circuit of the feedback circuit to output one of a plurality of reference voltages for controlling an amount of voltage delivered via the PFC output;

an energy storage device configured to store the electrical power received at the input during the first portion of the time interval;

an output configured to be coupled to a pulse-width modulator (PWM), wherein the output is configured to, during a second portion of the time interval, output the electrical power stored in the energy storage device during the first portion of the time interval; and a control terminal configured to receive, from a control device, a control signal to control operation of the energy storage device.

17. The power buffer of claim 16, wherein the energy storage device is configured to receive the electrical power as a direct current (DC) power from the PFC, and
wherein the power buffer further comprises a plurality of DC-to-DC converters, and
wherein the DC-to-DC converters are configured to adjust, based on the control signal received at the control terminal, an electrical parameter of the electrical power that is output during the second portion of the time interval.

18. The power buffer of claim 17, wherein the plurality of DC-to-DC converters comprise a first DC-to-DC converter and a second DC-to-DC converter,
wherein the first DC-to-DC converter is configured to step down DC voltage from the PFC, and
wherein the second DC-to-DC converter is configured to step up the DC power.

19. The power buffer of claim 16, wherein the control signal indicates an input parameter related to operation of a load to which the power buffer outputs the electrical power.

20. The power buffer of claim 16, further comprising a switch configured to actuate between a closed state and an open state responsive to an override signal from the control device,
wherein, in the closed state, the switch is configured to provide, to the energy storage device, the electrical power received from the PFC, and
wherein, in the open state, the switch is configured to prevent transmission, to the energy storage device, the electrical power received from the PFC.

* * * * *